(12) United States Patent
Nam et al.

(10) Patent No.: US 7,919,464 B2
(45) Date of Patent: Apr. 5, 2011

(54) USE OF A PEPTIDE THAT INTERACTS WITH αVβ3 INTEGRIN OF ENDOTHELIAL CELL

(75) Inventors: Ju-Ock Nam, Daegu (KR); Jung-Eun Kim, Daegu (KR); Ha-Won Jeong, Daegu (KR); Sung-Jin Lee, Daegu (KR); Byung-Heon Lee, Daegu (KR); Je-Yong Choi, Daegu (KR); Rang-Woon Park, Daegu (KR); Jae-Yong Park, Daegu (KR); In-San Kim, Daegu (KR)

(73) Assignee: Kyungpook National University Industry-Academic Cooperation Foundation, Daegu (KR)

(*) Notice: Subject to any disclaimer, the term of this patent is extended or adjusted under 35 U.S.C. 154(b) by 169 days.

(21) Appl. No.: 10/552,291

(22) PCT Filed: Apr. 2, 2004

(86) PCT No.: PCT/KR2004/000774
§ 371 (c)(1),
(2), (4) Date: Oct. 3, 2005

(87) PCT Pub. No.: WO2004/087193
PCT Pub. Date: Oct. 14, 2004

(65) Prior Publication Data
US 2007/0004622 A1    Jan. 4, 2007

(30) Foreign Application Priority Data

Apr. 3, 2003  (KR) .................. 10-2003-0021065

(51) Int. Cl.
*A61K 38/10*   (2006.01)
*A61K 38/16*   (2006.01)
(52) U.S. Cl. .......................................... 514/13; 514/12
(58) Field of Classification Search .................. None
See application file for complete search history.

(56) References Cited

U.S. PATENT DOCUMENTS
5,444,164 A   8/1995   Purchio et al.

FOREIGN PATENT DOCUMENTS
WO    WO 99/46282    * 3/1999

OTHER PUBLICATIONS

Zogakis et al. "General aspects of anti-angiogenesis and cancer therapy," Exp. Opin. Biol. Ther., 2001, 1, 253-75.*
Ribatti et al. "Angiogenesis and Anti-Angiogenesis in Hematological Malignancies," J. Hematotherapy & Stem Cell Res., 2003, 12, 11-22.*
Kerbel "Antiangiogenic Therapy: A Universal Chemosensitization Strategy for Cancer?" Science, 2006, 312, 1171-1175.*
Nam et al., "Identification of the αvβ3 Integrin-interacting Motif of βig-h3 and Its Anti-angiogenic Effect," *The Journal of Biological Chemistry*, 2003, vol. 278, n. 28, pp. 25902-25909, The American Society for Biochemistry and Molecular Biology, Inc., Washington, D.C.
Horton, The αvβ3 Integrin "Vitronectin Receptor," *Int. J. Biochem. Cell Biology*, 1997, vol. 29, n. 5, pp. 721-725, Elsevier Science Ltd., Great Britain.
Kim et al., "Identification of Motifs for Cell Adhesion with the Repeated Domains of Transforming Growth Factor-β-induced Gene, βig-h3," *The Journal of Biological Chemistry*, 2000, vol. 275, n. 40, The American Society for Biochemistry and Molecular Biology, Inc., Washington, D.C.
Kim et al., "Identification of Motifs in the Fasciclin Domains of the Transforming Growth Factor-β- induced Matrix Protein βig-h3 That Interact with the αvβ5 Integrin," *The Journal of Biological Chemistry*, 2002, vol. 277, n. 48, The American Society for Biochemistry and Molecular Biology, Inc., Washington, D.C.
Son, "Inhibitory mechanism of angiogenesis and tumorigenesis by βig-h3," Dissertation for Master's Degree of Medical Science of the Graduated School of Kyungpook University, submission date: Dec. 2005, publication date: Apr. 2006 (Abrstract).

* cited by examiner

*Primary Examiner* — Cecilia Tsang
*Assistant Examiner* — Christina Bradley
(74) *Attorney, Agent, or Firm* — Edwards Angell Palmer & Dodge LLP; Kongsik Kim, Esq.

(57) ABSTRACT

The present invention relates to the use of a peptide that interacts with the αvβ3 integrin of endothelial cells. More particularly, the invention relates to a method for inhibiting endothelial cell adhesion, endothelial cell migration and/or angiogenesis, using a peptide consisting of at least 18 amino acids, comprising tyrosine-histidine (TY) or asparagines-histidine (NH), and at least three hydrophobic amino acids with bulky side chains; or equivalents thereof. Furthermore, the invention provides a method for treating or preventing angiogenesis-related diseases, using the peptide.

10 Claims, 16 Drawing Sheets

Fig 1

| | | | |
|---|---|---|---|
| BIGH3_HUMAN | 161 | SNVNIEL...TDEIKHGMT 190 | (SEQ ID: 28) |
| BIGH3-PIG | 161 | SNVNIEL...TDEIKHGMA 190 | (SEQ ID: 29) |
| BIGH3_CHICK | 154 | SNVNIEL...TDDIKHGTT 183 | (SEQ ID: 30) |
| OSF2_MOUSE | 157 | NNVNVEL...TKDIKHGMV 186 | (SEQ ID: 31) |
| BIGH3_HUMAN | 298 | GDPEA...KSAMCAEAIVAGLS 326 | (SEQ ID: 32) |
| BIGH3-PIG | 298 | GDPEA...KSAMCAEAIVAGLS 326 | (SEQ ID: 33) |
| BIGH3_CHICK | 290 | GDPEA...KSAMCAEAIIAGLT 318 | (SEQ ID: 34) |
| OSF2_HUMAN | 292 | GDKVASEA...NTIQCSESIMGGAV 320 | (SEQ ID: 35) |
| OSF2_MOUSE | 294 | GDKVASEA...NTIQCSEAITGGAV 322 | (SEQ ID: 36) |
| BIGH3_HUMAN | 560 | GDAKEL...LGDEIIVSGGIGAIVR 588 | (SEQ ID: 37) |
| BIGH3-PIG | 560 | GDAKEL...VGDEIIVSGGIGAIVR 588 | (SEQ ID: 38) |
| BIGH3_CHICK | 552 | GNAKEL...FHMADEIIVSGAVSAIVR 580 | (SEQ ID: 39) |
| SLL1735 homolog | 59 | QNPPQ...TKDDIIKIGE 87 | (SEQ ID: 40) |
| SLL1735 | 59 | QNIPQ...VVAGKFTQADICRIST 87 | (SEQ ID: 41) |
| SLL1483 | 104 | PENKDK...VVPGKITAAQV-QSGE 132 | (SEQ ID: 42) |
| OSF2_HUMAN | 554 | RDKNA...LTPGVEIGKGFEPGVT 582 | (SEQ ID: 43) |
| OSF2_MOUSE | 556 | GDKNA...LTPGVVIGKGFEPGVT 584 | (SEQ ID: 44) |
| MP83_MYCTU | 164 | TDARL...IAGQ--ASPSRIDGT 190 | (SEQ ID: 45) |
| MPT83 | 145 | TDARL...IAGQ--ASPSRIDGT 171 | (SEQ ID: 46) |
| Q48948_MYCBO | 119 | TNSSL...VVAGQ--TSPANVVGT 145 | (SEQ ID: 47) |
| Q50769_MYCTU | 119 | TNSSL...VVAGQ--TSPANVVGT 145 | (SEQ ID: 48) |
| Putative secreted protein | 132 | NDRAQ...VVEHKKRITKAQIPHGT 160 | (SEQ ID: 49) |
| Fasciclin | 485 | EG-RGCASN...DLTFCSTATVPGAK 513 | (SEQ ID: 50) |
| HLC-32 | 284 | KDPAGK...ISDVKYSVSSSGQR 313 | (SEQ ID: 51) |
| Fasciclin | 775 | SKPADPM...VEDVVCCAGLIPTNW 803 | (SEQ ID: 52) |

| | | | |
|---|---|---|---|
| BIGH3_HUMAN | 432 | RNLLR.NHIIKDQLASKY...GQTIDTGGKTIR 464 | (SEQ ID: 53) |
| BIGH3_PIG | 432 | KNMLT.NHMIKDQLASKY...GQTIDTGGKTIR 464 | (SEQ ID: 54) |
| BIGH3_CHICK | 424 | KNLLL.NHIVKDQLSSKY...GQFIQTIGGKEIR 456 | (SEQ ID: 55) |
| OSF2_HUMAN | 426 | RLILQNHIIKVKVGLNE...GQIETIGGKQIR 458 | (SEQ ID: 56) |
| OSF2_MOUSE | 428 | RLILQNHIIKVKVGLND...GQIETIGGKQIR 460 | (SEQ ID: 57) |

FIG. 2
A
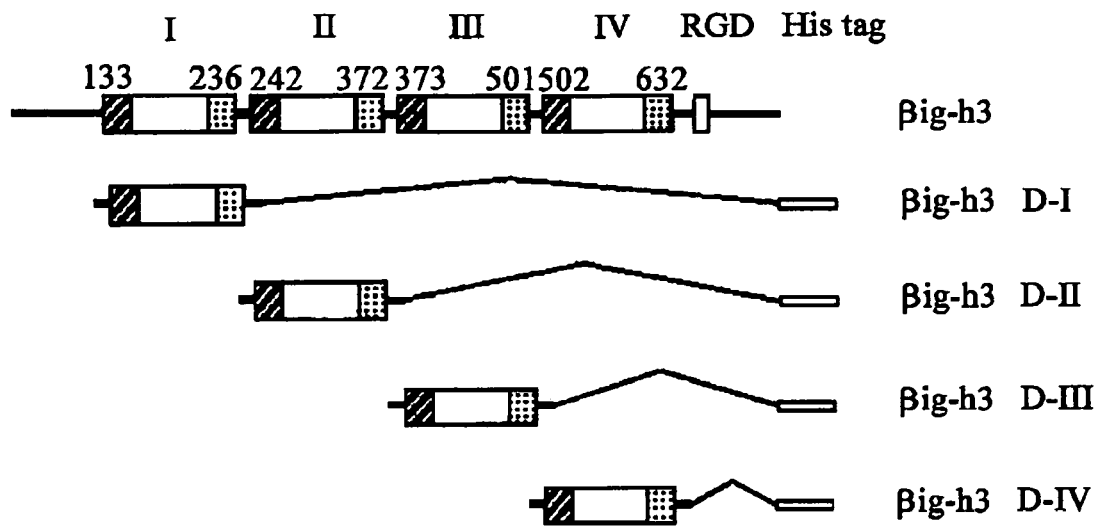
B
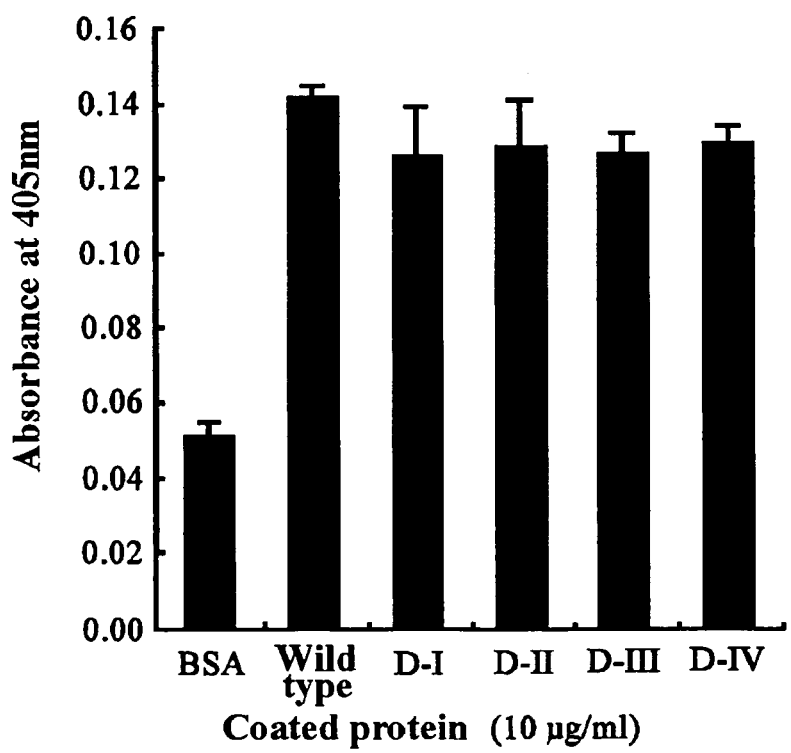

Fig 4b
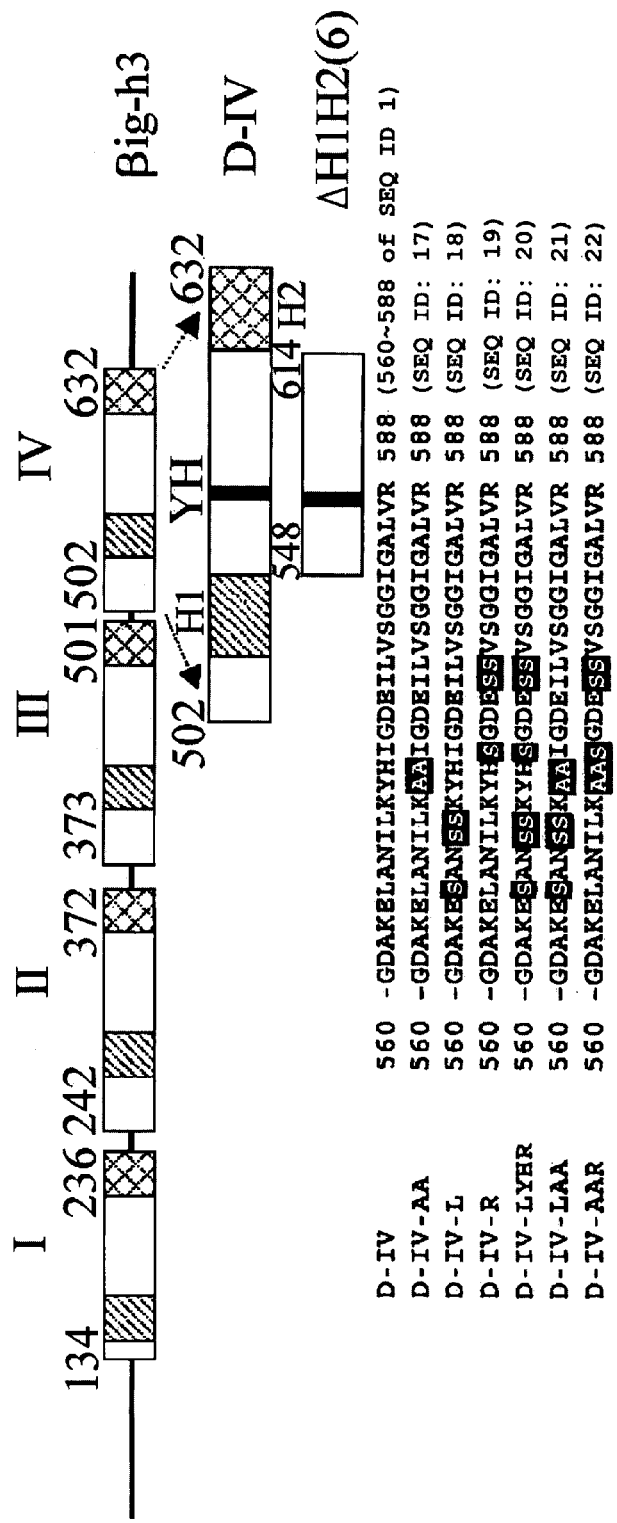
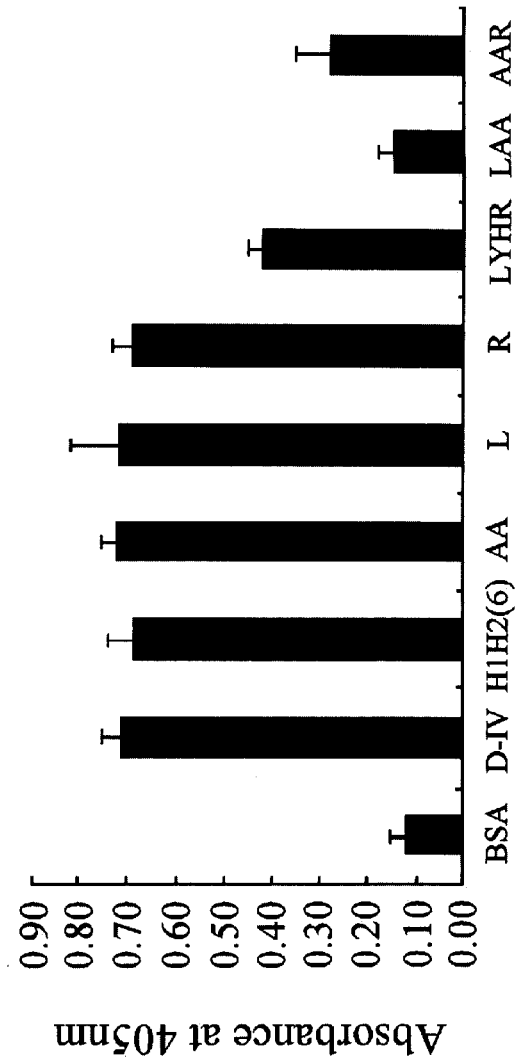

Fig7a
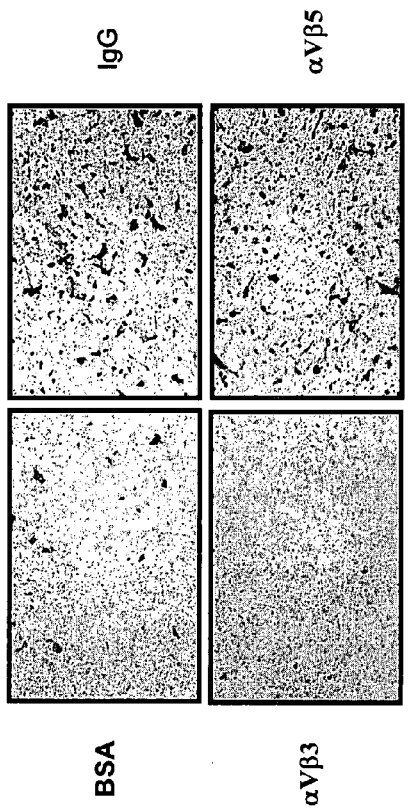
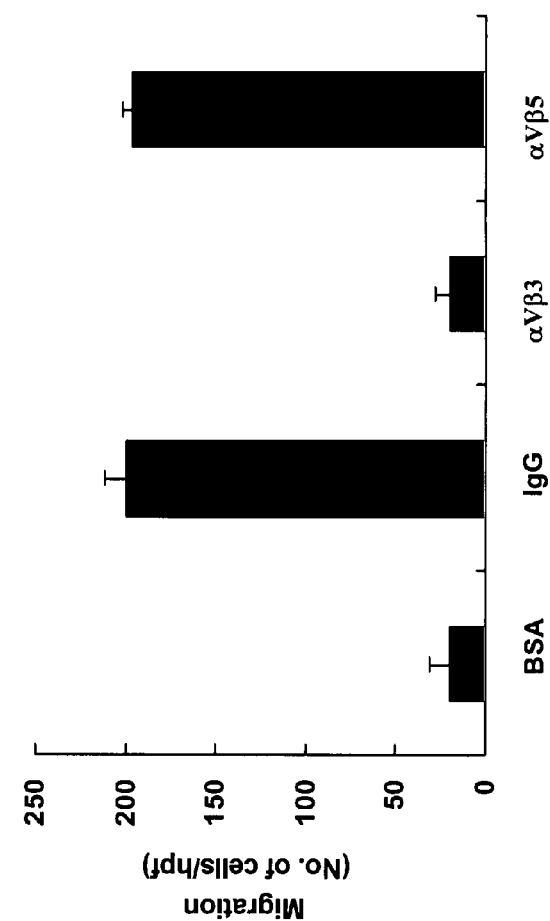

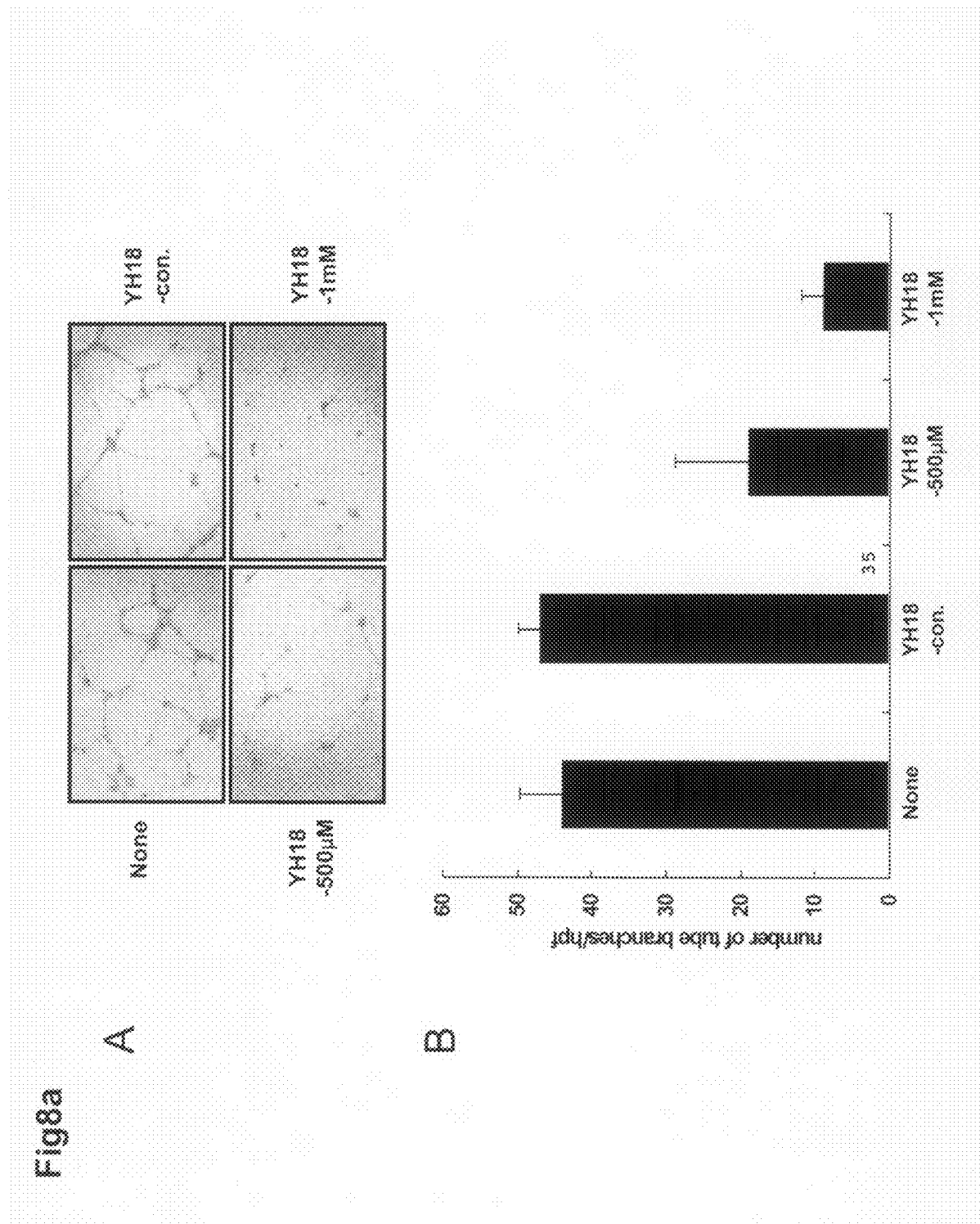

SEQUENCE LISTING

<160> NUMBER OF SEQ ID NOS: 57

<210> SEQ ID NO 1
<211> LENGTH: 683
<212> TYPE: PRT
<213> ORGANISM: Homo sapiens

<400> SEQUENCE: 1

```
Met Ala Leu Phe Val Arg Leu Leu Ala Leu Ala Leu Ala Leu
  1               5                  10                  15

Gly Pro Ala Ala Thr Leu Ala Gly Pro Ala Lys Ser Pro Tyr Gln Leu
             20                  25                  30

Val Leu Gln His Ser Arg Leu Arg Gly Arg Gln His Gly Pro Asn Val
             35                  40                  45

Cys Ala Val Gln Lys Val Ile Gly Thr Asn Arg Lys Tyr Phe Thr Asn
             50                  55                  60

Cys Lys Gln Trp Tyr Gln Arg Lys Ile Cys Gly Lys Ser Thr Val Ile
 65                  70                  75                  80

Ser Tyr Glu Cys Cys Pro Gly Tyr Glu Lys Val Pro Gly Glu Lys Gly
                 85                  90                  95

Cys Pro Ala Ala Leu Pro Leu Ser Asn Leu Tyr Glu Thr Leu Gly Val
                100                 105                 110

Val Gly Ser Thr Thr Thr Gln Leu Tyr Thr Asp Arg Thr Glu Lys Leu
            115                 120                 125

Arg Pro Glu Met Glu Gly Pro Gly Ser Phe Thr Ile Phe Ala Pro Ser
130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
                180                 185                 190

Ser Met Tyr Gln Asn Ser Asn Ile Gln Ile His His Tyr Pro Asn Gly
                195                 200                 205

Ile Val Thr Val Asn Cys Ala Arg Leu Leu Lys Ala Asp His His Ala
210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
                260                 265                 270

Gly Gln Tyr Thr Leu Leu Ala Pro Thr Asn Glu Ala Phe Glu Lys Ile
            275                 280                 285

Pro Ser Glu Thr Leu Asn Arg Ile Leu Gly Asp Pro Glu Ala Leu Arg
            290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
            340                 345                 350

Ser Asn Lys Asp Ile Leu Ala Thr Asn Gly Val Ile His Tyr Ile Asp
            355                 360                 365

Glu Leu Leu Ile Pro Asp Ser Ala Lys Thr Leu Phe Glu Leu Ala Ala
            370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
                405                 410                 415
```

-continued

Asn Ser Val Phe Lys Asp Gly Thr Pro Pro Ile Asp Ala His Thr Arg
            420                 425                 430

Asn Leu Leu Arg Asn His Ile Ile Lys Asp Gln Leu Ala Ser Lys Tyr
            435                 440                 445

Leu Tyr His Gly Gln Thr Leu Glu Thr Leu Gly Gly Lys Lys Leu Arg
        450                 455                 460

Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
                485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
            515                 520                 525

Glu Thr Leu Asn Arg Glu Gly Val Tyr Thr Val Phe Ala Pro Thr Asn
        530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Gly Ile Gly Ala Leu Val Arg Leu Lys Ser Leu
            580                 585                 590

Gln Gly Asp Lys Leu Glu Val Ser Leu Lys Asn Asn Val Val Ser Val
            595                 600                 605

Asn Lys Glu Pro Val Ala Glu Pro Asp Ile Met Ala Thr Asn Gly Val
        610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
                645                 650                 655

Ala Ser Ala Phe Ser Arg Ala Ser Gln Arg Ser Val Arg Leu Ala Pro
            660                 665                 670

Val Tyr Gln Lys Leu Leu Glu Arg Met Lys His
        675                 680

<210> SEQ ID NO 2
<211> LENGTH: 103
<212> TYPE: PRT
<213> ORGANISM: Homo sapiens

<400> SEQUENCE: 2

Gly Pro Gly Ser Phe Thr Ile Phe Ala Pro Ser Asn Glu Ala Trp Ala
1               5                   10                  15

Ser Leu Pro Ala Glu Val Leu Asp Ser Leu Val Ser Asn Val Asn Ile
            20                  25                  30

Glu Leu Leu Asn Ala Leu Arg Tyr His Met Val Gly Arg Arg Val Leu
        35                  40                  45

Thr Asp Glu Leu Lys His Gly Met Thr Leu Thr Ser Met Tyr Gln Asn
    50                  55                  60

Ser Asn Ile Gln Ile His His Tyr Pro Asn Gly Ile Val Thr Val Asn
65                  70                  75                  80

Cys Ala Arg Leu Leu Lys Ala Asp His His Ala Thr Asn Gly Val Val
                85                  90                  95

His Leu Ile Asp Lys Val Ile
            100

```
<210> SEQ ID NO 3
<211> LENGTH: 131
<212> TYPE: PRT
<213> ORGANISM: Homo sapiens

<400> SEQUENCE: 3

Asn Ile Gln Gln Ile Ile Glu Ile Glu Asp Thr Phe Glu Thr Leu Arg
  1               5                  10                  15

Ala Ala Val Ala Ala Ser Gly Leu Asn Thr Met Leu Glu Gly Asn Gly
                 20                  25                  30

Gln Tyr Thr Leu Leu Ala Pro Thr Asn Glu Ala Phe Glu Lys Ile Pro
             35                  40                  45

Ser Glu Thr Leu Asn Arg Ile Leu Gly Asp Pro Glu Ala Leu Arg Asp
         50                  55                  60

Leu Leu Asn Asn His Ile Leu Lys Ser Ala Met Cys Ala Glu Ala Ile
 65                  70                  75                  80

Val Ala Gly Leu Ser Val Glu Thr Leu Glu Gly Thr Thr Leu Glu Val
                 85                  90                  95

Gly Cys Ser Gly Asp Met Leu Thr Ile Asn Gly Lys Ala Ile Ile Ser
            100                 105                 110

Asn Lys Asp Ile Leu Ala Thr Asn Gly Val Ile His Tyr Ile Asp Glu
            115                 120                 125

Leu Leu Ile
        130

<210> SEQ ID NO 4
<211> LENGTH: 129
<212> TYPE: PRT
<213> ORGANISM: Homo sapiens

<400> SEQUENCE: 4

Pro Asp Ser Ala Lys Thr Leu Phe Glu Leu Ala Ala Glu Ser Asp Val
  1               5                  10                  15

Ser Thr Ala Ile Asp Leu Phe Arg Gln Ala Gly Leu Gly Asn His Leu
                 20                  25                  30

Ser Gly Ser Glu Arg Leu Thr Leu Leu Ala Pro Leu Asn Ser Val Phe
             35                  40                  45

Lys Asp Gly Thr Pro Pro Ile Asp Ala His Thr Arg Asn Leu Leu Arg
         50                  55                  60

Asn His Ile Ile Lys Asp Gln Leu Ala Ser Lys Tyr Leu Tyr His Gly
 65                  70                  75                  80

Gln Thr Leu Glu Thr Leu Gly Gly Lys Lys Leu Arg Val Phe Val Tyr
                 85                  90                  95

Arg Asn Ser Leu Cys Ile Glu Asn Ser Cys Ile Ala Ala His Asp Lys
            100                 105                 110

Arg Gly Arg Tyr Gly Thr Leu Phe Thr Met Asp Arg Val Leu Thr Pro
            115                 120                 125

Pro

<210> SEQ ID NO 5
<211> LENGTH: 131
<212> TYPE: PRT
<213> ORGANISM: Homo sapiens
```

```
<400> SEQUENCE: 5

Met Gly Thr Val Met Asp Val Leu Lys Gly Asp Asn Arg Phe Ser Met
1               5                   10                  15

Leu Val Ala Ala Ile Gln Ser Ala Gly Leu Thr Glu Thr Leu Asn Arg
            20                  25                  30

Glu Gly Val Tyr Thr Val Phe Ala Pro Thr Asn Glu Ala Phe Arg Ala
        35                  40                  45

Leu Pro Pro Arg Glu Arg Ser Arg Leu Leu Gly Asp Ala Lys Glu Leu
    50                  55                  60

Ala Asn Ile Leu Lys Tyr His Ile Gly Asp Glu Ile Leu Val Ser Gly
65                  70                  75                  80

Gly Ile Gly Ala Leu Val Arg Leu Lys Ser Leu Gln Gly Asp Lys Leu
                85                  90                  95

Glu Val Ser Leu Lys Asn Asn Val Val Ser Val Asn Lys Glu Pro Val
            100                 105                 110

Ala Glu Pro Asp Ile Met Ala Thr Asn Gly Val Val His Val Ile Thr
        115                 120                 125

Asn Val Leu
    130

<210> SEQ ID NO 6
<211> LENGTH: 85
<212> TYPE: PRT
<213> ORGANISM: Homo sapiens

<400> SEQUENCE: 6

Arg Ala Leu Pro Pro Arg Glu Arg Ser Arg Leu Leu Gly Asp Ala Lys
1               5                   10                  15

Glu Leu Ala Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45

Lys Leu Glu Val Ser Leu Lys Asn Asn Val Val Ser Val Asn Lys Glu
    50                  55                  60

Pro Val Ala Glu Pro Asp Ile Met Ala Thr Asn Gly Val Val His Val
65                  70                  75                  80

Ile Thr Asn Val Leu
                85

<210> SEQ ID NO 7
<211> LENGTH: 119
<212> TYPE: PRT
<213> ORGANISM: Homo sapiens

<400> SEQUENCE: 7

Met Gly Thr Val Met Asp Val Leu Lys Gly Asp Asn Arg Phe Ser Met
1               5                   10                  15

Leu Val Ala Ala Ile Gln Ser Ala Gly Leu Thr Glu Thr Leu Asn Arg
            20                  25                  30

Glu Gly Val Tyr Thr Val Phe Ala Pro Thr Asn Glu Ala Phe Arg Ala
        35                  40                  45

Leu Pro Pro Arg Glu Arg Ser Arg Leu Leu Gly Asp Ala Lys Glu Leu
    50                  55                  60

Ala Asn Ile Leu Lys Tyr His Ile Gly Asp Glu Ile Leu Val Ser Gly
65                  70                  75                  80

Gly Ile Gly Ala Leu Val Arg Leu Lys Ser Leu Gln Gly Asp Lys Leu
                85                  90                  95
```

```
Glu Val Ser Leu Lys Asn Asn Val Val Ser Val Asn Lys Glu Pro Val
            100                 105                 110

Ala Glu Pro Asp Ile Met Ala
            115
```

<210> SEQ ID NO 8
<211> LENGTH: 113
<212> TYPE: PRT
<213> ORGANISM: Homo sapiens

<400> SEQUENCE: 8

```
Met Gly Thr Val Met Asp Val Leu Lys Gly Asp Asn Arg Phe Ser Met
 1               5                  10                  15

Leu Val Ala Ala Ile Gln Ser Ala Gly Leu Thr Glu Thr Leu Asn Arg
            20                  25                  30

Glu Gly Val Tyr Thr Val Phe Ala Pro Thr Asn Glu Ala Phe Arg Ala
        35                  40                  45

Leu Pro Pro Arg Glu Arg Ser Arg Leu Leu Gly Asp Ala Lys Glu Leu
    50                  55                  60

Ala Asn Ile Leu Lys Tyr His Ile Gly Asp Glu Ile Leu Val Ser Gly
65                  70                  75                  80

Gly Ile Gly Ala Leu Val Arg Leu Lys Ser Leu Gln Gly Asp Lys Leu
                85                  90                  95

Glu Val Ser Leu Lys Asn Asn Val Val Ser Val Asn Lys Glu Pro Val
            100                 105                 110

Ala
```

<210> SEQ ID NO 9
<211> LENGTH: 73
<212> TYPE: PRT
<213> ORGANISM: Homo sapiens

<400> SEQUENCE: 9

```
Arg Ala Leu Pro Pro Arg Glu Arg Ser Arg Leu Leu Gly Asp Ala Lys
 1               5                  10                  15

Glu Leu Ala Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45

Lys Leu Glu Val Ser Leu Lys Asn Asn Val Val Ser Val Asn Lys Glu
    50                  55                  60

Pro Val Ala Glu Pro Asp Ile Met Ala
65                  70
```

<210> SEQ ID NO 10
<211> LENGTH: 67
<212> TYPE: PRT
<213> ORGANISM: Homo sapiens

<400> SEQUENCE: 10

```
Arg Ala Leu Pro Pro Arg Glu Arg Ser Arg Leu Leu Gly Asp Ala Lys
 1               5                  10                  15

Glu Leu Ala Asn Ile Leu Lys Tyr His Ile Gly Asp Glu Ile Leu Val
            20                  25                  30

Ser Gly Gly Ile Gly Ala Leu Val Arg Leu Lys Ser Leu Gln Gly Asp
        35                  40                  45
```

```
Lys Leu Glu Val Ser Leu Lys Asn Asn Val Val Ser Val Asn Lys Glu
    50                  55                  60

Pro Val Ala
 65

<210> SEQ ID NO 11
<211> LENGTH: 18
<212> TYPE: PRT
<213> ORGANISM: Artificial Sequence
<220> FEATURE:
<223> OTHER INFORMATION: D-IV-AA(18)

<400> SEQUENCE: 11

Lys Glu Leu Ala Asn Ile Leu Lys Ala Ala Ile Gly Asp Glu Ile Leu
  1               5                  10                  15

Val Ser

<210> SEQ ID NO 12
<211> LENGTH: 18
<212> TYPE: PRT
<213> ORGANISM: Artificial Sequence
<220> FEATURE:
<223> OTHER INFORMATION: D-IV-L(18)

<400> SEQUENCE: 12

Lys Glu Ser Ala Asn Ser Ser Lys Tyr His Ile Gly Asp Glu Ile Leu
  1               5                  10                  15

Val Ser

<210> SEQ ID NO 13
<211> LENGTH: 18
<212> TYPE: PRT
<213> ORGANISM: Artificial Sequence
<220> FEATURE:
<223> OTHER INFORMATION: D-IV-R(18)

<400> SEQUENCE: 13

Lys Glu Leu Ala Asn Ile Leu Lys Tyr His Ser Gly Asp Glu Ser Ser
  1               5                  10                  15

Val Ser

<210> SEQ ID NO 14
<211> LENGTH: 18
<212> TYPE: PRT
<213> ORGANISM: Artificial Sequence
<220> FEATURE:
<223> OTHER INFORMATION: D-IV-LYHR(18)

<400> SEQUENCE: 14

Lys Glu Ser Ala Asn Ser Ser Lys Tyr His Ser Gly Asp Glu Ser Ser
  1               5                  10                  15

Val Ser

<210> SEQ ID NO 15
<211> LENGTH: 18
<212> TYPE: PRT
<213> ORGANISM: Artificial Sequence
<220> FEATURE:
<223> OTHER INFORMATION: D-IV-LAA(18)

<400> SEQUENCE: 15

Lys Glu Ser Ala Asn Ser Ser Lys Ala Ala Ile Gly Asp Glu Ile Leu
  1               5                  10                  15

Val Ser
```

```
<210> SEQ ID NO 16
<211> LENGTH: 18
<212> TYPE: PRT
<213> ORGANISM: Artificial Sequence
<220> FEATURE:
<223> OTHER INFORMATION: D-IV-AAR(18)

<400> SEQUENCE: 16

Lys Glu Leu Ala Asn Ile Leu Lys Ala Ala Ser Gly Asp Glu Ser Ser
 1               5                  10                  15

Val Ser

<210> SEQ ID NO 17
<211> LENGTH: 29
<212> TYPE: PRT
<213> ORGANISM: Artificial Sequence
<220> FEATURE:
<223> OTHER INFORMATION: D-IV-AA

<400> SEQUENCE: 17

Gly Asp Ala Lys Glu Leu Ala Asn Ile Leu Lys Ala Ala Ile Gly Asp
 1               5                  10                  15

Glu Ile Leu Val Ser Gly Gly Ile Gly Ala Leu Val Arg
            20                  25

<210> SEQ ID NO 18
<211> LENGTH: 29
<212> TYPE: PRT
<213> ORGANISM: Artificial Sequence
<220> FEATURE:
<223> OTHER INFORMATION: D-IV-L

<400> SEQUENCE: 18

Gly Asp Ala Lys Glu Ser Ala Asn Ser Ser Lys Tyr His Ile Gly Asp
 1               5                  10                  15

Glu Ile Leu Val Ser Gly Gly Ile Gly Ala Leu Val Arg
            20                  25

<210> SEQ ID NO 19
<211> LENGTH: 29
<212> TYPE: PRT
<213> ORGANISM: Artificial Sequence
<220> FEATURE:
<223> OTHER INFORMATION: D-IV-R

<400> SEQUENCE: 19

Gly Asp Ala Lys Glu Leu Ala Asn Ile Leu Lys Tyr His Ser Gly Asp
 1               5                  10                  15

Glu Ser Ser Val Ser Gly Gly Ile Gly Ala Leu Val Arg
            20                  25

<210> SEQ ID NO 20
<211> LENGTH: 29
<212> TYPE: PRT
<213> ORGANISM: Artificial Sequence
<220> FEATURE:
<223> OTHER INFORMATION: D-IV-LYHR

<400> SEQUENCE: 20

Gly Asp Ala Lys Glu Ser Ala Asn Ser Ser Lys Tyr His Ser Gly Asp
 1               5                  10                  15

Glu Ser Ser Val Ser Gly Gly Ile Gly Ala Leu Val Arg
            20                  25
```

```
<210> SEQ ID NO 21
<211> LENGTH: 29
<212> TYPE: PRT
<213> ORGANISM: Artificial Sequence
<220> FEATURE:
<223> OTHER INFORMATION: D-IV-LAA

<400> SEQUENCE: 21

Gly Asp Ala Lys Glu Ser Ala Asn Ser Ser Lys Ala Ala Ile Gly Asp
 1               5                  10                  15

Glu Ile Leu Val Ser Gly Gly Ile Gly Ala Leu Val Arg
            20                  25

<210> SEQ ID NO 22
<211> LENGTH: 29
<212> TYPE: PRT
<213> ORGANISM: Artificial Sequence
<220> FEATURE:
<223> OTHER INFORMATION: D-IV-AAR

<400> SEQUENCE: 22

Gly Asp Ala Lys Glu Leu Ala Asn Ile Leu Lys Ala Ala Ser Gly Asp
 1               5                  10                  15

Glu Ser Ser Val Ser Gly Gly Ile Gly Ala Leu Val Arg
            20                  25

<210> SEQ ID NO 23
<211> LENGTH: 18
<212> TYPE: PRT
<213> ORGANISM: Artificial Sequence
<220> FEATURE:
<223> OTHER INFORMATION: D-I YH18

<400> SEQUENCE: 23

Ile Glu Leu Leu Asn Ala Leu Arg Tyr His Met Val Gly Arg Arg Val
 1               5                  10                  15

Leu Thr

<210> SEQ ID NO 24
<211> LENGTH: 18
<212> TYPE: PRT
<213> ORGANISM: Artificial Sequence
<220> FEATURE:
<223> OTHER INFORMATION: D-II YH18

<400> SEQUENCE: 24

Glu Ala Leu Arg Asp Leu Leu Asn Asn His Ile Leu Lys Ser Ala Met
 1               5                  10                  15

Cys Ala

<210> SEQ ID NO 25
<211> LENGTH: 18
<212> TYPE: PRT
<213> ORGANISM: Artificial Sequence
<220> FEATURE:
<223> OTHER INFORMATION: D-III YH18

<400> SEQUENCE: 25

Asp Gln Leu Ala Ser Lys Tyr Leu Tyr His Gly Gln Thr Leu Glu Thr
 1               5                  10                  15

Leu Gly
```

```
<210> SEQ ID NO 26
<211> LENGTH: 18
<212> TYPE: PRT
<213> ORGANISM: Artificial Sequence
<220> FEATURE:
<223> OTHER INFORMATION: D-IV YH18

<400> SEQUENCE: 26

Lys Glu Leu Ala Asn Ile Leu Lys Tyr His Ile Gly Asp Glu Ile Leu
 1               5                  10                  15

Val Ser

<210> SEQ ID NO 27
<211> LENGTH: 18
<212> TYPE: PRT
<213> ORGANISM: Artificial Sequence
<220> FEATURE:
<223> OTHER INFORMATION: YH18-con.

<400> SEQUENCE: 27

Lys Glu Leu Ala Asn Ile His Gly Ile Lys Leu Tyr Asp Glu Ile Leu
 1               5                  10                  15

Val Ser

<210> SEQ ID NO 28
<211> LENGTH: 30
<212> TYPE: PRT
<213> ORGANISM: Artificial Sequence
<220> FEATURE:
<223> OTHER INFORMATION: BIGH3_HUMAN

<400> SEQUENCE: 28

Ser Asn Val Asn Ile Glu Leu Leu Asn Ala Leu Arg Tyr His Met Val
 1               5                  10                  15

Gly Arg Arg Val Leu Thr Asp Glu Leu Lys His Gly Met Thr
                20                  25                  30

<210> SEQ ID NO 29
<211> LENGTH: 30
<212> TYPE: PRT
<213> ORGANISM: Artificial Sequence
<220> FEATURE:
<223> OTHER INFORMATION: BIGH3-PIG

<400> SEQUENCE: 29

Ser Asn Val Asn Ile Glu Leu Leu Asn Ala Leu Arg Tyr His Met Val
 1               5                  10                  15

Asp Arg Arg Val Leu Thr Asp Glu Leu Lys His Gly Met Ala
                20                  25                  30

<210> SEQ ID NO 30
<211> LENGTH: 30
<212> TYPE: PRT
<213> ORGANISM: Artificial Sequence
<220> FEATURE:
<223> OTHER INFORMATION: BIGH3_CHICK

<400> SEQUENCE: 30

Ser Asn Val Asn Ile Glu Leu Leu Asn Ala Leu Arg Tyr His Met Val
 1               5                  10                  15

Asn Lys Arg Val Leu Thr Asp Asp Leu Lys His Gly Thr Thr
                20                  25                  30
```

```
<210> SEQ ID NO 31
<211> LENGTH: 30
<212> TYPE: PRT
<213> ORGANISM: Artificial Sequence
<220> FEATURE:
<223> OTHER INFORMATION: OSF2_MOUSE

<400> SEQUENCE: 31

Asn Asn Val Asn Val Glu Leu Leu Asn Ala Leu His Ser His Met Val
 1               5                  10                  15

Asn Lys Arg Met Leu Thr Lys Asp Leu Lys His Gly Met Val
            20                  25                  30

<210> SEQ ID NO 32
<211> LENGTH: 29
<212> TYPE: PRT
<213> ORGANISM: Artificial Sequence
<220> FEATURE:
<223> OTHER INFORMATION: BIGH3_HUMAN

<400> SEQUENCE: 32

Gly Asp Pro Glu Ala Leu Arg Asp Leu Leu Asn Asn His Ile Leu Lys
 1               5                  10                  15

Ser Ala Met Cys Ala Glu Ala Ile Val Ala Gly Leu Ser
            20                  25

<210> SEQ ID NO 33
<211> LENGTH: 29
<212> TYPE: PRT
<213> ORGANISM: Artificial Sequence
<220> FEATURE:
<223> OTHER INFORMATION: BIGH3-PIG

<400> SEQUENCE: 33

Gly Asp Pro Glu Ala Leu Arg Asp Leu Leu Asn Asn His Ile Leu Lys
 1               5                  10                  15

Ser Ala Met Cys Ala Glu Ala Ile Val Ala Gly Leu Ser
            20                  25

<210> SEQ ID NO 34
<211> LENGTH: 29
<212> TYPE: PRT
<213> ORGANISM: Artificial Sequence
<220> FEATURE:
<223> OTHER INFORMATION: BIGH3_CHICK

<400> SEQUENCE: 34

Gly Asp Pro Glu Ala Leu Arg Asp Leu Leu Asn His His Ile Leu Lys
 1               5                  10                  15

Ser Ala Met Cys Ala Glu Ala Ile Ile Ala Gly Leu Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: OSF2_HUMAN

<400> SEQUENCE: 35

Gly Asp Lys Val Ala Ser Glu Ala Leu Met Lys Tyr His Ile Leu Asn
 1               5                  10                  15

Thr Leu Gln Cys Ser Glu Ser Ile Met Gly Gly Ala Val
            20                  25
```

```
<210> SEQ ID NO 36
<211> LENGTH: 29
<212> TYPE: PRT
<213> ORGANISM: Artificial Sequence
<220> FEATURE:
<223> OTHER INFORMATION: OSF2_MOUSE

<400> SEQUENCE: 36

Gly Asp Lys Val Ala Ser Glu Ala Leu Met Lys Tyr His Ile Leu Asn
 1               5                  10                  15

Thr Leu Gln Cys Ser Glu Ala Ile Thr Gly Gly Ala Val
            20                  25

<210> SEQ ID NO 37
<211> LENGTH: 29
<212> TYPE: PRT
<213> ORGANISM: Artificial Sequence
<220> FEATURE:
<223> OTHER INFORMATION: BIGH3_HUMAN

<400> SEQUENCE: 37

Gly Asp Ala Lys Glu Leu Ala Asn Ile Leu Lys Tyr His Ile Gly Asp
 1               5                  10                  15

Glu Ile Leu Val Ser Gly Gly Ile Gly Ala Leu Val Arg
            20                  25

<210> SEQ ID NO 38
<211> LENGTH: 29
<212> TYPE: PRT
<213> ORGANISM: Artificial Sequence
<220> FEATURE:
<223> OTHER INFORMATION: BIGH3-PIG

<400> SEQUENCE: 38

Gly Asn Ala Lys Glu Leu Ala Asn Ile Leu Lys Tyr His Val Gly Asp
 1               5                  10                  15

Glu Ile Leu Val Ser Gly Gly Ile Gly Ala Leu Val Arg
            20                  25

<210> SEQ ID NO 39
<211> LENGTH: 29
<212> TYPE: PRT
<213> ORGANISM: Artificial Sequence
<220> FEATURE:
<223> OTHER INFORMATION: BIGH3_CHICK

<400> SEQUENCE: 39

Gly Asn Ala Lys Glu Leu Ala Ser Ile Leu Lys Phe His Met Ala Asp
 1               5                  10                  15

Glu Ile Leu Val Ser Gly Ala Val Ser Ala Leu Val Arg
            20                  25

<210> SEQ ID NO 40
<211> LENGTH: 29
<212> TYPE: PRT
<213> ORGANISM: Artificial Sequence
<220> FEATURE:
<223> OTHER INFORMATION: SLL1735 homolog

<400> SEQUENCE: 40

Gln Asn Pro Pro Gln Leu Ala Arg Ile Leu Thr Tyr His Val Ala Ala
 1               5                  10                  15

Gly Arg Leu Thr Lys Asp Asp Leu Ile Lys Leu Gly Glu
            20                  25
```

```
<210> SEQ ID NO 41
<211> LENGTH: 29
<212> TYPE: PRT
<213> ORGANISM: Artificial Sequence
<220> FEATURE:
<223> OTHER INFORMATION: SLL1735

<400> SEQUENCE: 41

Gln Asn Ile Pro Gln Leu Ala Arg Ile Leu Thr Tyr His Val Val Ala
 1               5                  10                  15

Gly Lys Phe Thr Gln Ala Asp Leu Cys Arg Leu Ser Thr
            20                  25

<210> SEQ ID NO 42
<211> LENGTH: 29
<212> TYPE: PRT
<213> ORGANISM: Artificial Sequence
<220> FEATURE:
<223> OTHER INFORMATION: SLL1483

<400> SEQUENCE: 42

Pro Glu Asn Lys Asp Lys Leu Val Lys Ile Leu Thr Tyr His Val Val
 1               5                  10                  15

Pro Gly Lys Ile Thr Ala Ala Gln Val Gln Ser Gly Glu
            20                  25

<210> SEQ ID NO 43
<211> LENGTH: 29
<212> TYPE: PRT
<213> ORGANISM: Artificial Sequence
<220> FEATURE:
<223> OTHER INFORMATION: OSF2_HUMAN

<400> SEQUENCE: 43

Arg Asp Lys Asn Ala Leu Gln Asn Ile Ile Leu Tyr His Leu Thr Pro
 1               5                  10                  15

Gly Val Phe Ile Gly Lys Gly Phe Glu Pro Gly Val Thr
            20                  25

<210> SEQ ID NO 44
<211> LENGTH: 29
<212> TYPE: PRT
<213> ORGANISM: Artificial Sequence
<220> FEATURE:
<223> OTHER INFORMATION: OSF2_MOUSE

<400> SEQUENCE: 44

Gly Asp Lys Asn Ala Leu Gln Asn Ile Ile Leu Tyr His Leu Thr Pro
 1               5                  10                  15

Gly Val Tyr Ile Gly Lys Gly Phe Glu Pro Gly Val Thr
            20                  25

<210> SEQ ID NO 45
<211> LENGTH: 27
<212> TYPE: PRT
<213> ORGANISM: Artificial Sequence
<220> FEATURE:
<223> OTHER INFORMATION: MP83 MYCTU

<400> SEQUENCE: 45

Thr Asp Ala Lys Leu Leu Ser Ser Ile Leu Thr Tyr His Val Ile Ala
 1               5                  10                  15

Gly Gln Ala Ser Pro Ser Arg Ile Asp Gly Thr
            20                  25
```

```
<210> SEQ ID NO 46
<211> LENGTH: 27
<212> TYPE: PRT
<213> ORGANISM: Artificial Sequence
<220> FEATURE:
<223> OTHER INFORMATION: MPT83

<400> SEQUENCE: 46

Thr Asp Ala Lys Leu Leu Ser Ser Ile Leu Thr Tyr His Val Ile Ala
 1               5                  10                  15

Gly Gln Ala Ser Pro Ser Arg Ile Asp Gly Thr
            20                  25

<210> SEQ ID NO 47
<211> LENGTH: 27
<212> TYPE: PRT
<213> ORGANISM: Artificial Sequence
<220> FEATURE:
<223> OTHER INFORMATION: Q48948_MYCBO

<400> SEQUENCE: 47

Thr Asn Ser Ser Leu Leu Thr Ser Ile Leu Thr Tyr His Val Val Ala
 1               5                  10                  15

Gly Gln Thr Ser Pro Ala Asn Val Val Gly Thr
            20                  25

<210> SEQ ID NO 48
<211> LENGTH: 27
<212> TYPE: PRT
<213> ORGANISM: Artificial Sequence
<220> FEATURE:
<223> OTHER INFORMATION: Q50769_MYCTU

<400> SEQUENCE: 48

Thr Asn Ser Ser Leu Leu Thr Ser Ile Leu Thr Tyr His Val Val Ala
 1               5                  10                  15

Gly Gln Thr Ser Pro Ala Asn Val Val Gly Thr
            20                  25

<210> SEQ ID NO 49
<211> LENGTH: 29
<212> TYPE: PRT
<213> ORGANISM: Artificial Sequence
<220> FEATURE:
<223> OTHER INFORMATION: Putative Secreted protein

<400> SEQUENCE: 49

Asn Asp Arg Ala Gln Leu Lys Lys Val Leu Thr Tyr His Val Val Glu
 1               5                  10                  15

His Lys Lys Ile Thr Lys Ala Gln Leu Pro His Gly Thr
            20                  25

<210> SEQ ID NO 50
<211> LENGTH: 29
<212> TYPE: PRT
<213> ORGANISM: Artificial Sequence
<220> FEATURE:
<223> OTHER INFORMATION: Fasciclin

<400> SEQUENCE: 50

Glu Gly Arg Gly Cys Ala Ser Asn Ile Leu Lys Asn His Leu Leu Asp
 1               5                  10                  15

Leu Thr Phe Cys Ser Leu Ala Thr Val Pro Gly Ala Lys
            20                  25
```

-continued

```
<210> SEQ ID NO 51
<211> LENGTH: 30
<212> TYPE: PRT
<213> ORGANISM: Artificial Sequence
<220> FEATURE:
<223> OTHER INFORMATION: HLC-32

<400> SEQUENCE: 51

Lys Asp Pro Ala Gly Lys Leu Arg Asn Leu Leu Lys Tyr His Val Ile
 1               5                  10                  15

Ser Asp Val Lys Tyr Ser Val Ser Leu Ser Ser Gly Gln Arg
            20                  25                  30

<210> SEQ ID NO 52
<211> LENGTH: 29
<212> TYPE: PRT
<213> ORGANISM: Artificial Sequence
<220> FEATURE:
<223> OTHER INFORMATION: Fasciclin

<400> SEQUENCE: 52

Ser Lys Pro Ala Asp Pro Met Ala Leu Val Lys Thr His Ile Val Glu
 1               5                  10                  15

Asp Val Val Cys Cys Ala Gly Ile Ile Pro Thr Asn Trp
            20                  25

<210> SEQ ID NO 53
<211> LENGTH: 33
<212> TYPE: PRT
<213> ORGANISM: Artificial Sequence
<220> FEATURE:
<223> OTHER INFORMATION: BIGH3_HUMAN

<400> SEQUENCE: 53

Arg Asn Leu Leu Arg Asn His Ile Ile Lys Asp Gln Leu Ala Ser Lys
 1               5                  10                  15

Tyr Leu Tyr His Gly Gln Thr Leu Asp Thr Leu Gly Gly Lys Lys Leu
            20                  25                  30

Arg

<210> SEQ ID NO 54
<211> LENGTH: 33
<212> TYPE: PRT
<213> ORGANISM: Artificial Sequence
<220> FEATURE:
<223> OTHER INFORMATION: BIGH3_PIG

<400> SEQUENCE: 54

Lys Asn Leu Leu Leu Asn His Met Ile Lys Asp Gln Leu Ala Ser Lys
 1               5                  10                  15

Tyr Leu Tyr His Gly Gln Thr Leu Asp Thr Leu Gly Gly Lys Lys Leu
            20                  25                  30

Arg

<210> SEQ ID NO 55
<211> LENGTH: 33
<212> TYPE: PRT
<213> ORGANISM: Artificial Sequence
<220> FEATURE:
<223> OTHER INFORMATION: BIGH3_CHICK
```

-continued

```
<400> SEQUENCE: 55

Lys Asn Leu Leu Leu Asn His Ile Val Lys Asp Gln Leu Ser Ser Lys
  1               5                  10                  15

Tyr Leu Tyr His Gly Gln Lys Leu Gln Thr Leu Gly Asp Lys Glu Leu
             20                  25                  30

Arg

<210> SEQ ID NO 56
<211> LENGTH: 33
<212> TYPE: PRT
<213> ORGANISM: Artificial Sequence
<220> FEATURE:
<223> OTHER INFORMATION: OSF2_HUMAN

<400> SEQUENCE: 56

Lys Leu Ile Leu Gln Asn His Ile Leu Lys Val Lys Val Gly Leu Asn
  1               5                  10                  15

Glu Leu Tyr Asn Gly Gln Ile Leu Glu Thr Ile Gly Gly Lys Gln Leu
             20                  25                  30

Arg

<210> SEQ ID NO 57
<211> LENGTH: 33
<212> TYPE: PRT
<213> ORGANISM: Artificial Sequence
<220> FEATURE:
<223> OTHER INFORMATION: OSF2_MOUSE

<400> SEQUENCE: 57

Lys Leu Ile Leu Gln Asn His Ile Leu Lys Val Lys Val Gly Leu Asn
  1               5                  10                  15

Asp Leu Tyr Asn Gly Gln Ile Leu Glu Thr Ile Gly Gly Lys Gln Leu
             20                  25                  30

Arg
```

USE OF A PEPTIDE THAT INTERACTS WITH αVβ3 INTEGRIN OF ENDOTHELIAL CELL

TECHNICAL FIELD

The present invention relates to a peptide having an angiogenesis-inhibitory effect, and more particularly, to the anti-angiogenic use of a peptide that interacts with the αvβ3 integrin of endothelial cells.

BACKGROUND ART

Angiogenesis is defined as the formation of new capillary blood vessels from preexisting micro-vessels. Normal angiogenesis occurs during embryogenic development, tissue remodeling, organ growth, wound healing and female reproductive cycles (corpus luteum development) under tight physiological regulation (Folkman and Cotran, Int. Rev. Exp. Patho., 16:207-248, 1976). Generally, angiogenesis involves the proteolysis of the blood vessel basement membrane by proteases, followed by the migration, proliferation and differentiation of endothelial cells to form tubules and eventually the regeneration of new blood vessels.

Unregulated and abnormal angiogenesis may lead to various diseases. Examples of angiogenesis-related diseases that occur in pathological conditions include various cancers(tumors); vascular diseases such as vascular malformation, arteriosclerosis, vascular adhesions, and edematous sclerosis; ocular diseases such as corneal graft neovascularization, neovascular glaucoma, diabetic retinopathy, angiogenic corneal disease, macular degeneration, pterygium, retinal degeneration, retrolental fibroplasia and granular conjunctivitis; inflammatory diseases such as rheumatoid arthritis, systemic Lupus erythematosus and thyroiditis; and dermatological diseases such as psoriasis, capillarectasia, pyogenic granuloma, seborrheic dermatitis and acne (U.S. Pat. No. 5,994,292; Korean Patent Application Laid-Open No. 2001-66967; D'Amato R. J. et al., Ophtahlmol., 102:1261-1262, 1995; Arbiser J. L. J. Am. Acad. Derm., 34(3):486-497, 1996; O'Brien K. D. et al., Circulation, 93(4):672-682, 1996; Hanahan D. et al., Cell, 86:353-364, 1996).

Thus, studies on the mechanism of angiogenesis and the discovery of substances capable of inhibiting angiogenesis are of significant importance in the prevention and treatment of various diseases, including cancer. Current studies on the inhibition of angiogenesis are being performed on target genes by various strategies, including a strategy of administering a competitive substance to inhibit the action of VEGF and bFGF (basic fibroblast growth factor), which are known as potent inducers of angiogenesis, and a strategy of regulating the expression of integrin in vascular endothelial cells to inhibit the metastasis of the cancer cells. Regarding the relationship of angiogenesis with cancer, studies on the correlation between vascular absorption and angiogenesis induced by cancer cells and on proteins that induce angiogenesis are being performed but are still large incomplete. Studies on angiogenic inhibition are applicable to the diagnosis, treatment and/or prevention of a variety of angiogenesis-related diseases, and thus, there is a continued need for research and development regarding angiogenesis.

Meanwhile, βig-h3 that is an extracellular matrix protein was first isolated by differential screening of a cDNA. library made from a human lung adenocarcinoma cell line (A549) that had been treated with TGF-β1 (Skonier J. et al., DNA Cell Biol., 11:511-522, 1992). The βig-h3 protein consists of 683 amino acids and contains an amino-terminal secretory sequence and a carboxy-terminal RGD (Arg-Gly-Asp) motif serving as a ligand recognition site for several integrins (Skonier, J. et al., DNA Cell Biol., 11:511, 1992). Also, the βig-h3 protein contains four homologous internal repeat domains (designated "fas-1 domains") which are homologous to similar motifs in the *Drosophila* fasciclin-I protein. Such fas-1 domains have highly conserved sequences found in the secretory and membrane proteins of many organisms, including mammals, insects, sea urchins, plants, yeast, and bacteria (Kawamoto T., et al., Biochim. Biophys. Acta, 288-292, 1998). Each of the fas-1 domains consists of 110-140 amino acids and comprises two highly conserved branches of about 10 amino acids (H1 and H2).

The βig-h3 protein is known to have a fibrillar structure and to interact with several extracellular matrix proteins such as fibronectin and collagen (Kim J.-E., et al., Invest. Ophthalmol. Vis. Sci., 43:656-661, 2002). Furthermore, the βig-h3 protein has been reported to be involved in cell growth and differentiation, and wound healing and morphogenesis (Skonier J., et al., DNA Cell Biol., 13:571-584, 1994; Dieudonne S. C., et al., J. Cell. Biochem., 76:231-243, 1999; Kim J.-E., et al., J. Cell. Biochem., 77:169-178, 2000; Rawe I. M., et al., Invest. Ophthalmol. Vis. Sci., 38:893-900, 1997; and LeBaron R G., et al., J. Invest. Dermatol., 104:844-849, 1995). In addition, the βig-h3 protein is known to mediate the adhesion of many different cell types, including corneal epithelial cells, chondrocytes and fibroblasts (LeBaron R. G., et al., J. Invest. Dermatol., 104:844-849, 1995; Ohno S., et al., Biochim. Biophys. Acta, 1451: 196-205, 1999; and Kim J.-E., et al., J. Biol. Chem., 275:30907-30915, 2000). However, there is still no report indicating that the βig-h3 protein is involved in angiogenesis.

DISCLOSURE OF THE INVETION

Accordingly, the present inventors have performed extensive studies to determine whether the βig-h3 protein is involved in angiogenesis, and consequently, found that YH motif conserved in the fas-1 domains of the βig-h3 protein shows an anti-angiogenic effect through the αvβ3 integrin of endothelial cells, thereby completing the present invention.

Therefore, an object of the present invention is to provide the novel use of a peptide that interacts with the αvβ3 integrin of endothelial cells.

To achieve the above object, in one aspect, the present invention provides a method of inhibiting endothelial cell adhesion, endothelial cell migration and/or angiogenesis, comprising administering to a subject in need thereof an effective amount of a peptide that interacts with the αvβ3 integrin of endothelial cells.

In another aspect, the present invention provides a method of treating or preventing angiogenesis-related diseases, comprising administering to a subject in need thereof an effective amount of a peptide that interacts with the αvβ3 integrin of endothelial cells.

In yet another aspect, the present invention provides a pharmaceutical composition for the inhibition of angiogenesis or for the treatment or prevention of angiogenesis-related diseases, comprising as active ingredient a peptide that interacts with the αvβ3 integrin of endothelial cells.

In still another aspect, the present invention provides the use of a peptide interacting with the αvβ3 integrin of endothelial cells, for the preparation of a pharmaceutical agent for the inhibition of endothelial cell adhesion, endothelial cell migration and/or angiogenesis.

In another further aspect, the present invention provides the use of a peptide interacting with the αvβ3 integrin of endothelial cells, for the preparation of an agent for the treatment or prevention of angiogenesis-related diseases.

As used herein, the term "YH motif" is defined as an amino acid sequence comprising tyrosine-histidine (Y—H) or asparagine-histidine (N—H) residues highly conserved in the fas-1 domains of a βig-h3 protein, and flanking several hydrophobic amino acid residues adjacent to the conserved residues(e.g., leucine and isoleucine) (Kim, J.-E. et al., J. Biol. Chem., 277:4615946465, 2002). The YH motif is also highly conserved in fas-1 domains derived from other proteins in addition to the βig-h3 protein (see FIG. 1).

As used herein, the term "effective amount" is defined as an amount at which the effect of inhibiting endothelial cell migration, endothelial cell adhesion and/or angiogenesis is shown.

As used herein, the term "subject" means animals, including mammals, particularly human beings. The subject may preferably be a patient who requires treatment.

Herein after, the present invention will be described in detail.

A peptide according to the present invention may consist of at least 18 amino acids, comprising tyrosine-histidine (Y—H) or asparagine-histidine (N—H) residues, and at least three hydrophobic amino acids with bulky side chains. The hydrophobic amino acids with bulky side chains may be leucines (L) or isoleucines (I). The inventive peptide comprises at least three of the hydrophobic amino acids, preferably four to six of them. The hydrophobic amino acids are preferably adjacent to the tyrosine-histidine (Y—H) or asparagines-histidine (N—H) residue. Concretely, the hydrophobic amino acids may be located at one side (N-terminal or C-terminal region) or both sides of the tyrosine-histidine (Y—H) or asparagines-histidine (N—H) residues.

Concretely, the inventive peptide may have an amino acid sequence comprising the YH motif which is conserved in the fas-1 domains. The inventive peptide may preferably consist of at least 18 amino acids, comprising the YH motif derived from each of the fas-1 domains of the βig-3 protein. More preferably, the inventive peptide may comprises an amino acid sequence represented by (I, D, E or K)-(E, A or Q)-L-(L, R or A)-(N, D or S)-(A, L, K or I)-(L or Y)-(R, N, L or K)-(Y or N)-H-(M, I or G)-(V, L, Q or G)-(G, K, T or D)-(R, S, L or E)-(R, A, E or I)-(V, M, T or L)-(L, C or V)-(T, A, G or S). The amino acid abbreviations as described above have the following definitions: I, isoleucine; D, aspartate; E, glutamate; K, lysine; A, alanine; Q, glutamine; L, leucine; R, arginine; N, asparagine; S, serine; Y, tyrosine; H, histidine; M, methionine; G, glycine; V, valine; T, threonine; and C, cysteine. Most preferably, the inventive peptide may comprise an amino acid sequence selected from the group consisting of SEQ ID NO: 23 to SEQ ID NO: 26. The amino acid sequence of SEQ ID NO: 23 is derived from the first fas-1 domain of the βig-h3 protein, and the amino acid sequence of SEQ ID NO: 24 from the second fas-1 domain of the βig-h3 protein, the amino acid sequence of SEQ ID NO: 25 from the third fas-1 domain of the βig-h3 protein, and the amino acid sequence of SEQ ID NO: 26 from the fourth fas-1 domain of the βig-h3 protein.

It is understood that functional equivalents or salts of the peptide consisting of at least 18 amino acids, comprising tyrosine-histidine (Y—H) or asparagine-histidine (N—H) residues and at least three hydrophobic amino acids with bulky side chains, are within the scope of the inventive peptide. As used herein, the term "functional equivalents" is defined as peptides where some amino acids in the inventive peptide are mutated to such a degree that they do not influence the physiological activity of the peptides. In other words, the peptides having the same or similar structure as the inventive peptide as well as amino acid sequences are within the scope of the present invention insofar as they show substantially the same physiological activity as that of the inventive peptide. As used herein, the term "physiological activity" means the activity of inhibiting endothelial cell adhesion, endothelial cell migration and/or angiogenesis by the interacting with the αvβ3 integrin of endothelial cells.

The mutation as described above includes the substitution, deletion and/or addition of amino acids, and may be preferably the substitution of amino acids. An example of this mutation is the case where the hydrophobic amino acids with bulky side chains adjacent to the tyrosine-histidine (Y—H) or asparagine-histidine (N—H) on the YH motif are substituted with other amino acids, and preferably serine. More preferably, the inventive peptide may also have either an amino acid sequence selected from the group consisting of SEQ ID NO: 12 to SEQ ID NO: 14, or an amino acid sequence selected from the group consisting of SEQ ID NO: 18 to SEQ ID NO: 20, which comprises the amino acid sequence selected from SEQ ID NO: 12 to SEQ ID NO: 14.

The mutation may also be the case where the tyrosine-histidine (Y—H) or asparagine-histidine (N—H) on the YH motif is substituted with two other amino acids. Preferably, the tyrosine (Y) or asparagine (N) may be substituted with one selected from the group consisting of serine (S), histidine (H), phenylalanine (F) and threonine (T), and/or the histidine may be substituted with asparagine (N). More preferably, the tyrosine-histidine (Y—H) or asparagine-histidine (N—H) may be substituted with amino acids selected from the group consisting of serine-histidine (S—H), histidine-histidine (H—H), phenylalanine-histidine (F—H), threonine-histidine (T-H) and tyrosine-asparagine (Y—N), which are conserved in the fas-1 domains of proteins known in the prior art (see FIG. 1).

Moreover, the tyrosine-histidine (Y—H) or asparagine-histidine (N—H) may also be substituted with hydrophobic amino acids, and preferably alanine-alanine (A-A). In this case, the inventive peptide may have either an amino acid sequence of SEQ ID NO: 11, or an amino acid sequence of SEQ ID NO: 17, which comprises the amino acid sequence of SEQ ID NO: 11.

In addition, the mutation also includes the case where both the tyrosine-histidine (Y—H) or asparagine-histidine (N—H) and the flanking hydrophobic amino acids with bulky side chains are substituted as described above. In this case, however, the hydrophobic amino acids with bulky side chains are preferably present at least three within the inventive peptide. Preferably, the inventive peptide may have either an amino acid sequence of SEQ ID NO: 15 or SEQ ID NO: 16, or an amino acid sequence of SEQ ID NO: 21 or SEQ ID NO: 22, which comprises the amino acid sequence of SEQ ID NO: 15 or SEQ ID NO: 16.

Furthermore, the scope of the functional equivalents according to the present invention also encompasses peptide derivatives obtained by partially modifying the chemical structure of the inventive peptide while maintaining the backbone and physiological activity of the inventive peptide. Examples thereof include structural modifications to modify the stability, storage, volatility and solubility of the inventive peptide.

The inventive peptide may be easily prepared by a chemical synthesis method known in the art (Creighton, Proteins; Structures and Molecular Principles, W. H. Freeman and Co., NY, 1983). Typical methods includes but are not limited to liquid or solid state synthesis, fragment condensation, and F-MOC or T-BOC chemistry (Chemical Approaches to the Synthesis of Peptides and Proteins, Williams et al., Eds., CRC Press, Boca Raton Fla., 1997; A Practical Approach, Atherton & Sheppard, Eds., IRL Press, Oxford, England, 1989).

Moreover, the inventive peptide may be prepared by a genetic engineering method. For this purpose, a DNA sequence encoding the inventive peptide is constructed according to a conventional method. The DNA sequence can be constructed by PCR-amplification with suitable primers. Alternately, the DNA sequence may also be synthesized by any standard method known in the art, for example, using an automated DNA synthesis system (sold from Biosearch or Applied Biosystems). The constructed DNA sequence is inserted into a vector containing one or more expression control sequences (e.g., promoter and enhancer, etc.) which are operatively linked to the DNA sequence to control the expression of the DNA sequence. Host cells are then transfected with the resulting recombinant expression vector. The transfected cells are incubated in a suitable medium and condition to express the DNA sequence, and a substantially pure peptide encoded by the DNA sequence is recovered. The peptide recovery may be performed by a method known in the art (e.g., chromatography). As used herein, the term "substantially pure peptide" means that the inventive peptide does not substantially contain any peptides derived from host cells. For the genetic engineering method for synthesizing the inventive peptide, reference may be made to the following publications: Maniatis et al., Molecular Cloning; A laboratory Manual, Cold Spring Harbor laboratory, 1982; Sambrook et al., supra; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

Previously, the present inventors reported that the βig-h3 protein has both α3β1 integrin-interacting motif that induces the adhesion of epithelial cells (Kim, J.-E. et al., J. Biol. Chem., 275:30907-30915, 2000), and αvβ5 integrin-interacting motif that mediates the adhesion of fibroblasts (Kim, J.-E. et al., J. Biol. Chem., 277:46159-46165, 2002). Then, in the present invention, whether the βig-h3 protein and its fas-1 domains have endothelial cell adhesion activity was examined, and an integrin receptor that is involved in the adhesion of endothelial cells by the βig-h3 protein was identified. Furthermore, to discover a motif within the βig-h3 protein that interacts with the integrin receptor, deletion mutants of the βig-h3 protein were prepared and their fragments, which are involved in cell adhesion, were examined (see Examples 1 to 4-1).

The results showed that the βig-h3 protein and each of its fas-1 domains mediate the adhesion of endothelial cells at almost equal activity with each other (see FIG. 2), and that the αvβ3 integrin is involved in the adhesion of endothelial cells by interacting with the βig-h3 protein (see FIGS. 3a to 3d). Furthermore, it was found that amino acids 548-614 (ΔH1H2 (6)) of SEQ ID NO: 1, which corresponds to a fragment of the fas-1 domains, have activity related to the cell adhesion (see FIG. 4b).

Meanwhile, the present inventors previously reported that an YH motif that binds to the αvβ5 integrin was present within a fragment corresponding to amino acids 548-614 of the βig-h3 protein (Kim, L. E. et al., J. Biol. Chem., 277: 46159-46165, 2002). Thus, to confirm that the YH motif mediates endothelial cell adhesion by interacting with the αvβ3 integrin, the present inventors constructed a fragment of 29 amino acids (amino acids 560-588 of SEQ ID NO: 1) comprising the YH motif, and relevant mutants whose tyrosine-histidine residues and flanking several isoleucines/ leucines were substituted with alanine-alanine residues and serines, respectively, and examined their cell adhesion activity (see Example 4-2).

The results revealed that although various mutants of the YH motif have somewhat different activities, they all retain the activity of mediating the cell adhesion (see FIG. 4b).

Then, on the basis of the sequence of each fas-1 domain of the βig-h3 protein, the present inventors synthesized four peptides (YH18 synthetic peptides represented by SEQ ID NOs: 23 to 26) consisting of 18 amino acids, which were designed to comprise the YH motif. The effect of the synthesized peptides on the adhesion of endothelial cells was tested (see Example 5).

The results showed that the YH18 synthetic peptides inhibit endothelial cell adhesion, which is mediated by the βig-h3 protein, in a dose-dependent manner (see FIG. 5). This suggests that YH motif that is a conserved sequence in the fas-1 domains is responsible for endothelial cell adhesion to βig-h3 protein through the αvβ3 integrin.

Furthermore, in the present invention, whether or not the YH motif is involved in the migration of endothelial cells in addition to the adhesion of endothelial cells was tested (see FIG. 7). The results revealed that the YH18 synthetic peptide inhibits endothelial cell migration, which is promoted by the βig-h3 protein, in a dose-dependent manner (see FIGS. 7a and 7b).

Additionally, in the present invention, whether or not the YH motif that inhibits endothelial cell adhesion and migration shows an anti-angiogenic effect was tested (see Example 8). The results showed that angiogenesis is effectively inhibited by the YH18 synthetic peptide both in vivo and in vitro (see FIGS. 8a and 8b).

The peptide according to the present invention has the following physiological activities:

First, the inventive peptide interacts with the αvβ3 integrin of endothelial cells.

Second, it inhibits the adhesion and migration of endothelial cells.

Third, it inhibits angiogenesis both in vitro and in vivo.

Accordingly, the present invention provides a pharmaceutical composition for the inhibition of endothelial cell adhesion, endothelial cell migration and/or angiogenesis, comprising the inventive peptide as an active ingredient. Also, the present invention provides a pharmaceutical composition for the treatment or prevention of angiogenesis-related diseases, comprising the inventive peptide as an active ingredient.

The angiogenesis-related diseases that can be treated or prevented according to the present invention include various cancers(tumors); vascular diseases such as hemangioma, angiofibroma, vascular malformation, arteriosclerosis, vascular adhesions, and edematous sclerosis; ocular diseases such as corneal graft neovascularization, neovascular glaucoma, diabetic retinopathy, angiogenic corneal disease, macular degeneration, pterygium, retinal degeneration, retrolental fibroplasia and granular conjunctivitis; inflammatory diseases such as rheumatoid arthritis, systemic Lupus erythematosus and thyroiditis; and dermatological diseases, such as psoriasis, capillarectasia, pyogenic granuloma, seborrheic dermatitis and acne (U.S. Pat. No. 5,994,292; Korean Patent Application Laid-Open No. 2001-66967; D'Amato R. J. et al., Ophtahlmol., 102:1261-1262, 1995; Arbiser J. L. J. Am. Acad. Derm., 34(3):486-497, 1996; O'Brien K. D. et al., Circulation, 93(4):672-682, 1996; Hanahan D. et al., Cell, 86:353-364, 1996). More preferred examples include cancers, arthritis, psoriasis, diabetic eye diseases, arteriosclerosis, and inflammation.

The pharmaceutical composition comprising the inventive peptide as an active ingredient may further comprise a pharmaceutically acceptable carrier, for example, a carrier for oral or parenteral administration. Examples of the carrier for oral administration include lactose, starch, cellulose derivatives, magnesium stearate, and stearic acid. For oral administration, the inventive peptide may be mixed with an excipient and used in various forms, including enteric tablets, buccal tablets, troches, capsules, elixirs, suspensions, syrups and wafers. Also, examples of the carrier for parenteral administration includes water, suitable oils, saline solution, aqueous glucose and glycol, and the inventive composition may further comprise stabilizers and conservatives. Suitable examples of the stabilizers include antioxidants, such as sodium hydrogensulfite, sodium bisulfite and ascorbic acid. Suitable examples of the preservatives include benzalkonium chloride, methyl- or propyl-paraben, and chlorobutanol. For other pharmaceutically acceptable carriers, reference may be made to the following literature: Remington's Pharmaceutical Sciences, 19th ed., Mack Publishing Company, Easton, Pa., 1995.

The pharmaceutical composition according to the present invention may be formulated in various forms for oral or parenteral administration. The formulations for parenteral administration are typically injection formulations, and preferably isotonic aqueous solution or suspension. The injection formulations may be prepared using suitable dispersing or wetting agents, and suspending agents, according to any technique known in the art. For example, the components may be formulated for injection by dissolving them in a saline or buffer solution. Examples of the formulations for oral administration include tablets and capsules, and these formulations may comprise diluents (e.g., lactose, dextrose, sucrose, mannitol, sorbitol, cellulose, and/or glycin) and lubricants (e.g., silica, talc, stearic acid and magnesium or calcium salts thereof, and/or polyethylene glycol), in addition to the active ingredient. The tablets may comprise binders such as magnesium aluminum silicate, starch paste, gelatin, tragacanth, methyl cellulose, sodium carboxymethylcellulose and/or polyvinylpyrrolidone, and occasionally, it may further comprise disintegrants such as starch, agar, alginate or a sodium salt thereof, absorbing agents, coloring agents, flavoring agents and/or sweetening agents on a case by case basis. These formulations may be prepared by a conventional method such as mixing, granulation or coating.

The pharmaceutical composition according to the present invention may additionally comprise aids such as preservatives, wettable powders, emulsifiers, salts for the regulation of osmotic pressure, and/or buffers, and other therapeutically useful materials. The pharmaceutical composition may be formulated according to a conventional method.

The total amount of the inventive peptide as an active ingredient in the inventive pharmaceutical composition can be administered to a subject as a single dose over a relatively short period of time, or can be administered using a fractionated treatment protocol where multiple doses are administered over a prolonged period of time. Although the content of the inventive peptide in the inventive pharmaceutical composition can vary depending on the severity of diseases, the inventive peptide can be generally administered several times a day at a dose of 10 µg-10 mg. However, the dose of the inventive peptide depends on many factors, including the age, weight, general health, sex, disease severity, diet and excretion of a subject, as well as the route of administration and the number of treatments to be administered. In view of these factors, any person skilled in the art would adjust the particular dose so as to obtain an effective dose for inhibiting angiogenesis, or for treating or preventing angiogenesis-related diseases. The pharmaceutical composition according to the present invention is not specifically limited in its formulation, administration route and administration mode insofar as it shows the effects of the present invention.

BRIEF DESCRIPTION OF THE DRAWINGS

FIG. 1 shows the comparison between amino acid sequences which contain the tyrosine-histidine residues that are highly conserved in fas-1 domains derived from various proteins, and the conserved leucine/isoleucine residues adjacent to the tyrosin-histidine residues.

FIG. 2 is a schematic diagram (A) showing recombinant proteins containing each fas-1 domain of a βig-h3 protein, and a graphic diagram (B) showing the adhesion of HUVECs to the plate coated with βig-h3 or each of its fas-1 domains, in terms of absorbance.
BSA: bovine serum albumin as control
Wild-type: recombinant βig-h3 His-β-b protein containing all of four fas-1 domains.
D-I: first fas-1 domain
D-II: second fas-1 domain
D-III: third fas-1 domain
D-IV: fourth fas-1 domain

FIG. 4b schematically shows various substitution mutants of an YH motif conserved in the fourth fas-1 domain, and graphically shows test results for the HUVECs adhesion activity of the mutants.
Black blocks: substituted amino acids.

FIG. 7a is a photograph (A) and a graphic diagram (B), which show the inhibition of HUVECs migration toward βig-h3 coated on the plate by a function-blocking antibody against αvβ3 or αvβ5 integrin.
    BSA: plate coated with BSA
    IgG: treated with mouse IgG
    αvβ3: treated with LM609 (antibody to αvβ3)
    αvβ5: treated with P1F6 (antibody to αvβ5)

FIG. 8a is a photograph (A) showing the inhibition of HUVECs tube formation by an YH18 synthetic peptide, and a graphic diagram (B) showing the result of measurement for the number of tube branches formed.
    Control: treated with 5% DMSO
    YH18-con.: treated with YH18-con. peptide (control peptide)
    YH18-500 µM: treated with 500 µM YH18 synthetic peptide
    YH18-1 mM: treated with 1 mM YH18 synthetic peptide

BEST MODE FOR CARRYING OUT THE INVENTION

Figure 3A:
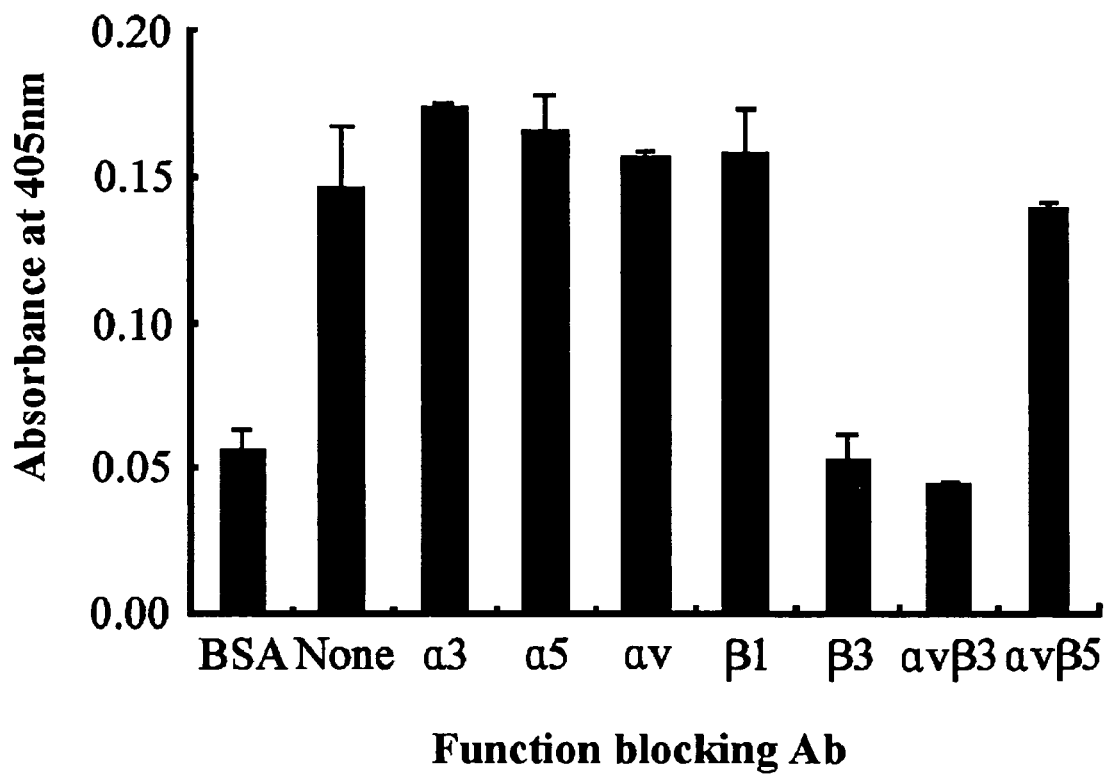
FIG. 3a is a graphic diagram showing the inhibition of HUVECs adhesion to the βig-h3 coated on the plate by function-blocking antibodies against various integrins.
BSA: plate coated with BSA
None: no treatment
α3: treated with P1B5 (antibody to α3)
α5: treated with P1D6 (antibody to α5)
αv: treated with P3G8 (antibody to αv)
β1: treated with 6S6 (antibody to β1)
β3: treated with B3A (antibody to β3)
αvβ3: treated with LM609 (antibody to αvβ3)
αvβ5: treated with P1F6 (antibody to αvβ5)

Hereinafter, the present invention will be described in detail by examples. It will however be obvious to a person skilled in the art that the present invention is not limited to or by the examples.

EXAMPLE 1

Expression and Purification of βig-h3 Protein and its fas-1 Domains 1-1: Construction of Expression Vector Previously, the present inventors reported recombinant proteins comprising βig-h3 and each of its fas-1 domains (Kim, J.-E. et al., J. Biol. Chem., 275:30907-30915, 2000; and Korean Patent Registration No.10-0382042). Thus, βig-h3 and its fas-1 domains were prepared in the same manner as described in the report.

Concretely, a recombinant human βig-h3 protein (hereinafter, referred to as "βig-h3 His-β-b") that expresses all of four fas-1 domains was prepared using a pHis-β-b vector. The pHis-β-b vector had been prepared by inserting an Asp718-BglII fragment (obtained by partially deleting the amino terminal region of βig-h3 cDNA) into the EcoRV/EcoRI sites of pET-29β. Also, to express recombinant proteins containing each fas-1 domain of human βig-h3, the present inventors PCR-amplified four cDNA fragments of βig-h3, which include the first fas-1 domain (βig-h3 D-I), the second fas-1 domain (βig-h3 D-II), the third fas-1 domain (βig-h3 D-III) or the fourth fas-1 domain (βig-h3 D-IV), respectively (see A of FIG. 2).

Then, each of the PCR products was cloned into the EcoRV/XhoI sites of a pET-29b(+) vector (Novagen; Madison, Wis.). The constructed expression vectors were named "pβig-h3 D-I", "pβig-h3 D-II", "pβig-h3 D-III" and "pβig-h3 D-IV", respectively. The amino acid sequences of the four fas-1 domains of βig-h3 are represented by SEQ ID NO: 2 to SEQ ID NO: 5, respectively.

1-2: Transformation of E. coli and Purification of Recombinant Protein

E. coli BL21 (DE3) cells were transformed with each of the expression vectors constructed in Example 1-1. The transformed E. coli cells were incubated in LB medium containing 50 µg/ml kanamycin. To induce the expression of each recombinant protein, when the absorbance of the culture reached 0.5-0.6 at a 595 nm, the culture was added with 1 mM IPTG (isopropyl-β-D-(−)-thiogalactopyranoside) and further incubated at 37° C. for three hours. Next, purification of the expressed proteins was performed according to the method described by Kim, J.-E. et al., J. Cell. Biochem., 77:169-187, 2000. For this purpose, the cells were collected by centrifugation and resuspended in buffer (50 mM Tris-HCl (pH 8.0), 100 mM NaCl, 1 mM EDTA, 1% Triton X-100, 1 mM PMSF, 0.5 mM DTT). The cell suspension was disrupted by sonication. The proteins expressed in the form of an inclusion body were dissolved in an 8M urea-denaturation buffer, and the denaturated proteins were purified with a Ni—NTA resin (Qiagen). The recombinant proteins were eluted in 200 mM imidazole solution, and purified by dialysis against 20 mM Tris-HCl buffer containing 50 mM sodium chloride in a stepwise manner from high to low urea concentration. The expressed and purified proteins were analyzed by SDS-PAGE (data not shown). Unlike the recombinant protein βig-h3 His-β-b containing all of the four fas-1 domains, the recombinant proteins containing each of the four fas-1 domains were synthesized in a water-soluble form and thus did not require a modification step. Also, they could be easily obtained in large amounts.

Meanwhile, the E. coli transformed with the expression vectors pHis-β-b, pβig-h3 D-II and pβig-h3 D-IV were termed "E. coli BL21/His-β-b", "E. coli BL21/Hisβ-g" and "E. coli BL21/Hisβ-e", respectively, and deposited in the Korean Collection for Type Cultures (KCTC), Korean Research Institute of Bioscience and Biotechnology, under accession numbers KCTC 18008P, KCTC 18010P and KCTC 18009P, respectively, on Apr. 25, 2000.

EXAMPLE 2

Test of Endothelial Cell Adhesion Activity of βig-h3 and its fas-1 Domains

Cell adhesion assay was performed according to the method described by Kim, J.-E. et al., J. Biol. Chem., 277:

4615946165, 2002. For this purpose, 10 μg/ml of each of the recombinant proteins (βig-h3 His-β-b, βig-h3 D-I, βig-h3 D-II, βig-h3 D-III and βig-h3 D-IV) prepared in Example 1 was placed into a flat-bottomed 96-well ELISA (enzyme-linked immunosorbent assay) plate (Costar, Corning Inc., NY) and then incubated overnight at 4° C., to coat the surface of the plate. As a control, 2% BSA was coated on the plate. Then, the plate was treated with PBS (phosphate-buffered saline) containing 2% BSA, and blocked at room temperature for one hour.

Meanwhile, HUVECs (human umbilical vein endothelial cells; Clonetics, San Diego, Calif.) were incubated in EGM medium (Clonetics, San Diego, Calif.) containing 2% FBS (Fetal Bovine Serum) under a condition of 37° C. and 5% $CO_2$. The incubated cells were suspended in medium at a density of $3\times10^5$ cells/ml, and 0.1 ml of the cell suspension was added to each well of the plate. Next, the cells were incubated at 37° C. for 30 minutes and washed one time with PBS buffer to remove cells which had not been attached to the plate. Attached cells were added with 50 mM citrate buffer (pH 5.0) containing 3.75 mM p-nitrophenyl-N-acetyl β-D-glycosaminide and 0.25% Triton X-100, and incubated at 37° C. for one hour. Thereafter, 50 mM glycine buffer (pH 10.4) containing 5 mM EDTA was added to block the activity of the enzyme. The absorbance was measured at a 405-nm in a Bio-Rad model 550 microplate reader. Here, the higher the number of cells adhered to the plate, the higher the absorbance.

The results showed that, as shown in B of FIG. 2, βig-h3 mediated the adhesion of endothelial cells, and each of the fas-1 domains of βig-h3 also mediated the adhesion of endothelial cells with an almost equal activity to that of βig-h3.

EXAMPLE 3

Identification of Integrins that are Involved in Adhesion of Endothelial Cells to βig-h3

3-1: Test 1 for Identification of Integrin Receptors

To identify integrins that are involved in the adhesion of endothelial cells to βig-h3, the present inventors have performed a cell adhesion inhibition assay using various antibodies that specifically blocks the function of integrins.

For this purpose, 5 μg/ml of monoclonal antibodies specific to different types of integrin (Chemicon, International Inc, Temecula, Calif.) was preincubated at 37° C. for 30 minutes with HUVECs in 0.1 ml of the cell suspension ($3\times10^5$ cells/ml). The following antibodies were used in this test: P1B5 (antibody to α3), P1D6 (antibody to α5), P3G8 (antibody to αv), 6S6 (antibody to β1), B3A (antibody to β3), LM609 (antibody to αvβ3) and P1F6 (antibody to αvβ5). A culture which had not been preincubated with the antibody was used as a control. Then, the incubated cells were transferred onto plates precoated with the recombinant protein βig-h3 His-β-b and incubated at 37° C. for 30 minutes. The attached cells were then quantified in the same manner as in Example 2. The results showed that, as shown in FIG. 3a, the adhesion of endothelial cells to βig-h3 was inhibited specifically by the antibodies to αvβ3 integrin and β3 integrin, but it was not inhibited by the antibodies to other integrins, including α3 and α5.

3-2: Test 2 for Identification of Integrin Receptors

In Example 2 above, it was confirmed that βig-h3 and also its fas-1 domains mediate the adhesion of endothelial cells. Thus, in order to identify an integrin receptor for each of the fas-1 domains of βig-h3, the present inventors coated a plate surface with each of the fas-1 domains of βig-h3 and performed a cell adhesion inhibition assay.

Figure 3B:
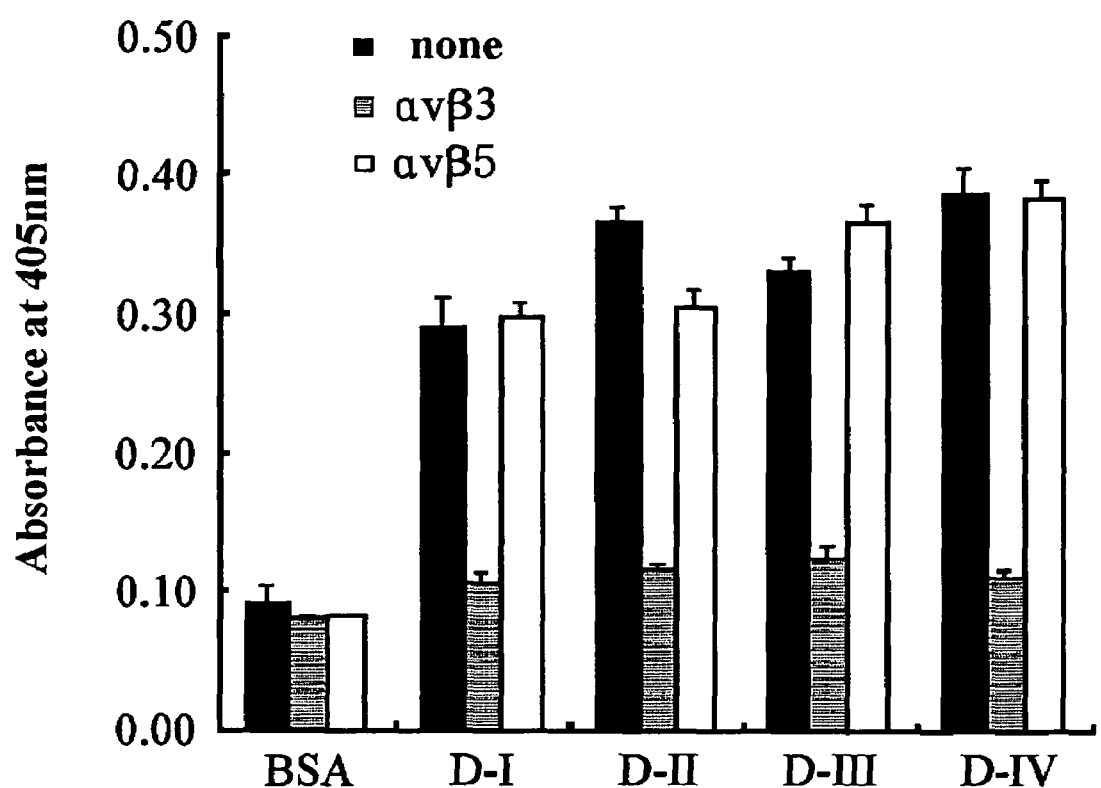
FIG. 3b is a graphic diagram showing the inhibition of HUVECs adhesion to each of fas-1 domains coated on the plate by a function-blocking antibody against αvβ3 or αvβ5 integrin.
BSA: plate coated with BSA
D-I: first fas-1 domain of βig-h3
D-II: second fas-1 domain of βig-h3
D-III: third fas-1 domain of βig-h3
D-IV: fourth fas-1 domain of βig-h3

The results showed that, as shown in FIG. 3b, the adhesion of endothelial cells to each of the fas-1 domains was inhibited specifically by the antibody to αvβ3, but it is not inhibited by the antibody to αvβ5.

3-3: Confirmation of Integrins that are Expressed on Surface of Endothelial Cells To confirm that HUVECs express both αvβ3 and αvβ5 integrin on their surface, the present inventors performed an FACS analysis using monoclonal antibodies specific to the two integrins.

For this purpose, a plate in which HUVECs had been grown to confluence was treated with PBS buffer containing 0.25% trypsin and 0.05% EDTA to detach the cells from the plate surface. The cells were washed two times with PBS buffer and resuspended in PBS buffer. The cell suspension was added with an anti-αvβ3 integrin antibody (LM609; Chemicon, International Inc, Temecula, Calif.) or an anti-αvβ5 integrin antibody (PIF6; Chemicon, International Inc, Temecula, Calif.) and incubated at 4° C. for one hour. The cells were then further incubated for one hour at 4° C. with 10 μg/ml of a FITC-conjugated secondary goat antimouse IgG antibody (Santa Cruz Biotechnology, Inc., Calif.). The resulting cells were analyzed at 488 nm on the flow cytometer FACSCalibur system (Becton Dickinson, San Jose, Calif.) equipped with a 5-watt laser. A control was incubated with a secondary antibody alone.

Figure 3C:
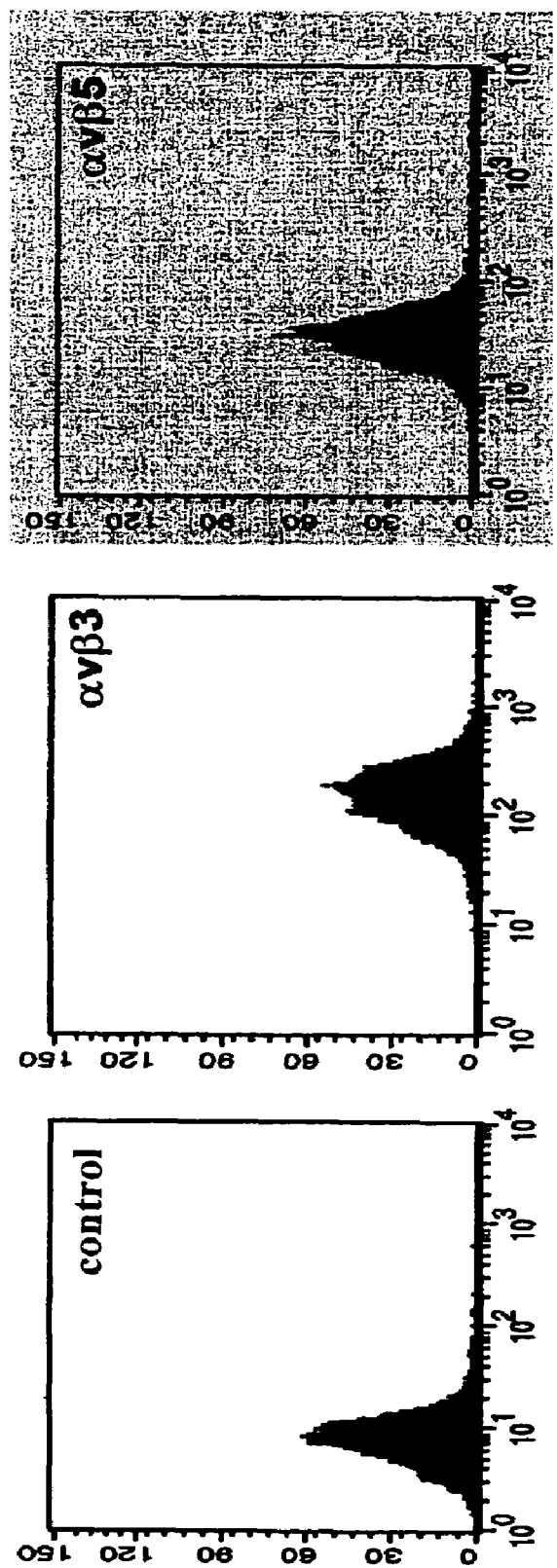
FIG. 3c shows the results of FACS analysis for the expression of integrin on the HUVECs surface using a function-blocking antibody against αvβ3 or αvβ5 integrin.

The results showed that, as shown in FIG. 3c, HUVECs expressed both the αvβ3 integrin and the αvβ5 integrin. However, the expression level of the αvβ5 integrin was far less than that of the αvβ3 integrin.

3-4: Test 3 for Identification of Integrin Receptors

To confirm that HUVECs adhesion that is mediated by βig-h3 depends on αvβ3 integrin, the present inventors tested the binding affinity of βig-h3 in the presence of an antibody that specifically blocks the function of the integrin. This binding assay was performed according to the method described by Maile, L. A., et al., J. Biol. Chem., 275:23745-23750, 2002.

First, HUVECs were suspended in medium at a density of $1\times10^5$ cells/ml. 1 ml of the cell suspension was preincubated with anti-αvβ3 antibody (LM609) or anti-αvβ5 antibody (P1F6) at 37° C. for 30 minutes. Thereafter, the preincubated cells were incubated with biotinylated βig-h3 (hereinafter, referred to as "biotin-βig-h3") in a serum-free medium containing 0.1% BSA at 4° C. for 5 hours. The biotin-βig-h3 was added at concentrations of $1\times10^{-10}$, $1\times10^{-9}$ and $5\times10^{-9}$ μm, respectively. Then, the cells were washed three times with PBS buffer (pH 7.4), and dissolved at 4° C. in ice-cold buffer A (10 mM Tris-Cl, pH 7.4, 150 mM NaCl, 1% Nonidet P-40, 1% sodium deoxycholate, 0.5% SDS, 0.02% sodium azide, 1 mM EDTA, 1 mM phenylmethylsulfonyl fluoride). The cell lysates were clarified by centrifugation at 13,000 rpm for 30 minutes at 4° C. Equal amounts of protein were then separated by SDS-PAGE, 8% gel. The amount of biotin-βig-h3 was determined by Western immuno-blotting.

To visualize the biotin-βig-h3, the membranes were incubated with HRP (hoseradish peroxidase; Amersham Biosciences)-conjugated streptavidin. Next, Binding of the peroxidase-labeled antibody was visualized using ELC (enhanced chemiluminesence; Amersham Biosciences). As an internal control, a β-tubulin protein was subjected to Western blotting to verify equal protein loading.

Figure 3D:
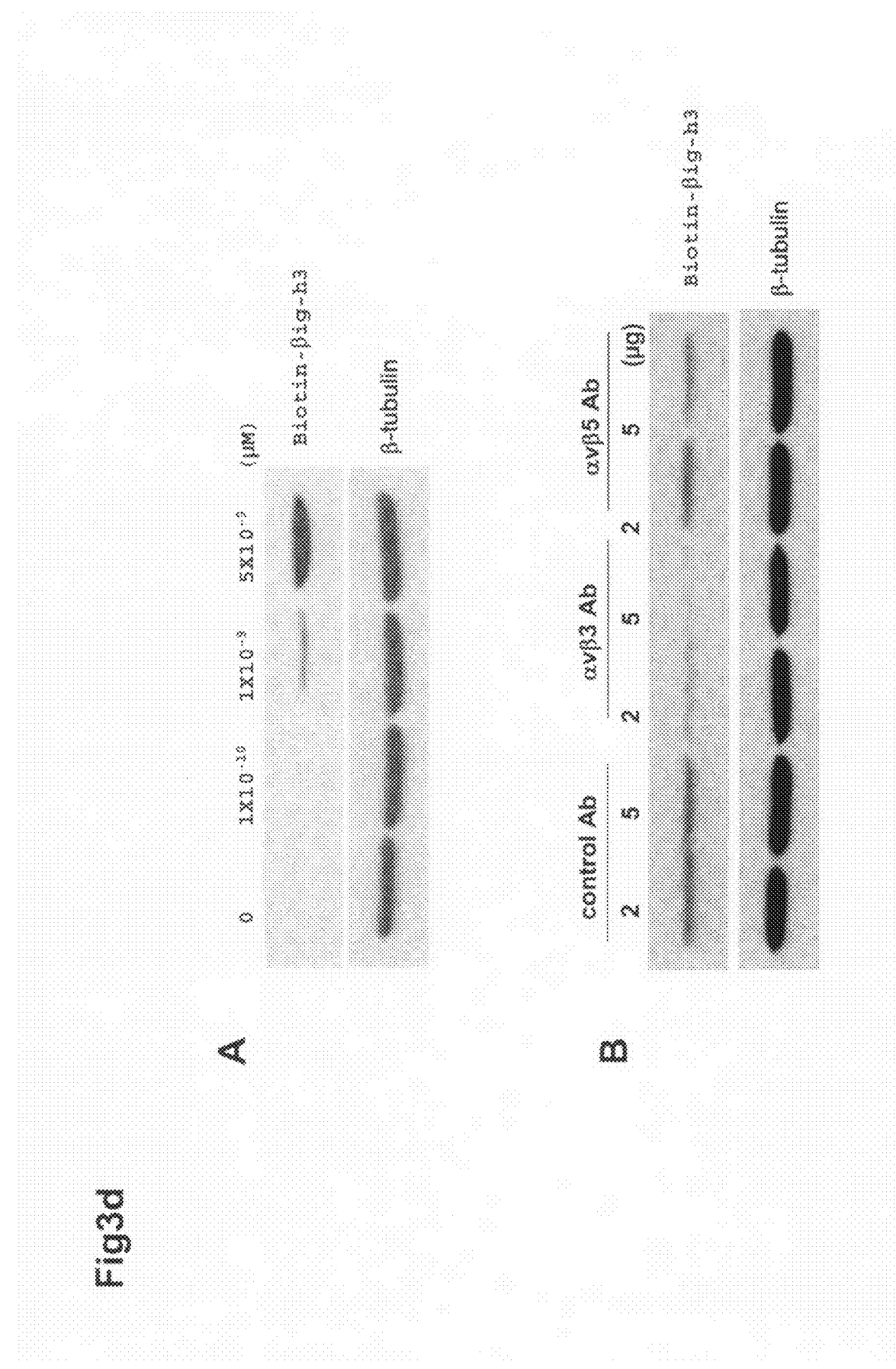
FIG. 3d shows the results of dose-dependent Western-immunoblotting analysis for the binding ability of biotin-βig-h3 to a HUVECs cell membrane (A), and for the inhibition of biotin βig-h3 binding to the HUVECs cell membrane by a function-blocking antibody against αvβ3 or αvβ5 integrin (B), in which the concentration-dependent Western-immunoblotting analysis is performed to identify a receptor for βig-h3 that is involved in endothelial cell adhesion. β-tubulin is an internal control for equal protein loading.

The results showed that βig-h3 was bound to HUVECs surface in a dose-dependent manner (see A of FIG. 3d), and its binding was specifically inhibited only by the antibody to αvβ3 integrin (see B of FIG. 3d).

Such results suggest that each of the fas-1 domains of βig-h3 contains a motif that mediates the adhesion of endothelial cells through the 'αvβ3 integrin', but not the αvβ5 integrin.

EXAMPLE 4

Identification of βig-h3 Motif Interacting with αvβ3 on Endothelial Cell Adhesion 4-1: Identification of αvβ3 Integrin-Interacting Motifs Using Deletion Mutants of fas-1 Domains To identify motifs that interact with the αvβ3 integrin when βig-h3 or its fas-1 domains induce the adhesion of endothelial cells by interacting with the αvβ3 intergrin, the present inventors prepared deletion mutants of the fas-1 domains and tested their cell adhesion activity.

Figure 4A:
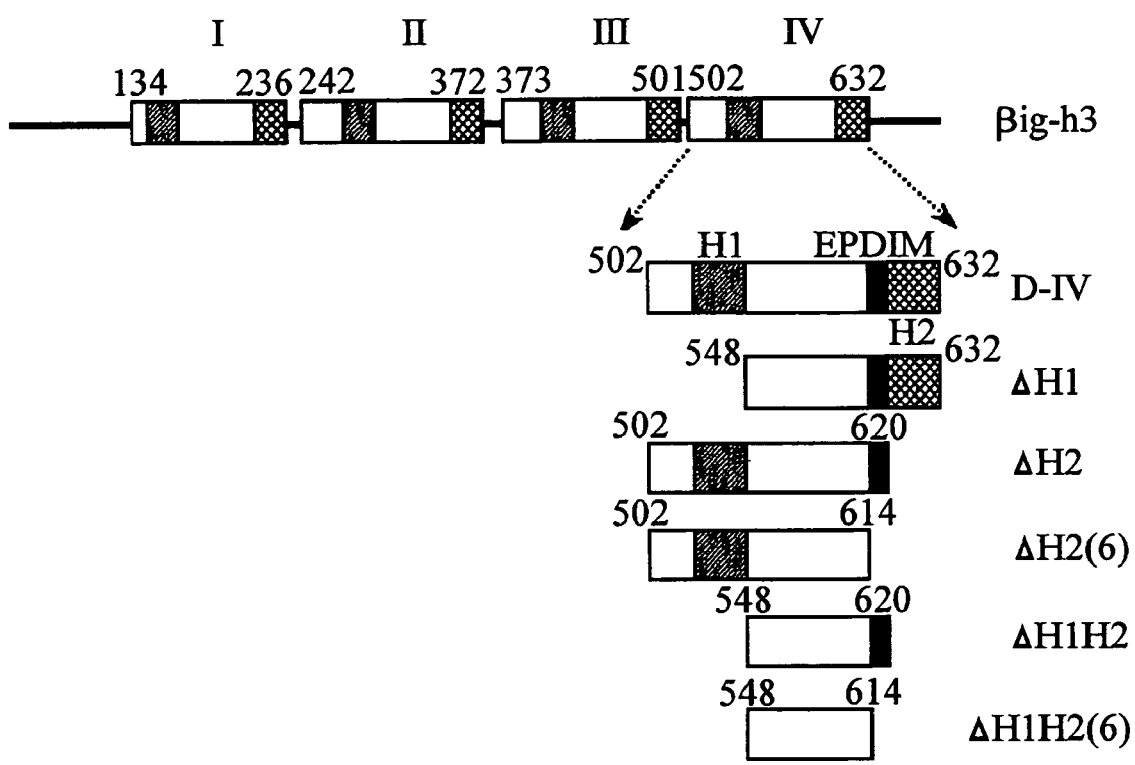
FIG. 4a is a schematic diagram showing various deletion mutants of the fourth fas-1 domain (D-IV) of βig-h3.

For this purpose, deletion mutants of the fas-1 domains were prepared according to the method described by Kim, J.-E. et al., J. Biol. Chem., 275:30907-30915, 2000. Concretely, in the present invention, there were prepared several deletion mutant fragments which lack a H1 or H2 peptide, which is highly conserved in the fas-1 domains, and/or an EPDIM motif, which is involved in the adhesion of corneal epithelial cells by interacting with the α3β1 integrin (see FIG. 4a). Information of the deletion mutant fragments is given in Table 1 below. The amino acid region of each of the deletion mutant fragments is based on the amino acid sequence of βig-h3, which is represented by SEQ ID NO: 1.

TABLE 1

Deletion mutants of fas-1 domains

| No. | Amino acid region of deletion mutant fragment | Designation | Characteristic | SEQ ID NO |
|---|---|---|---|---|
| 1 | 548-632 | ΔH1 | 5'-terminal fragment containing H1 peptide was deleted. | 6 |
| 2 | 502-620 | ΔH2 | H2 peptide was deleted. | 7 |
| 3 | 502-614 | ΔH2(6) | EPDIM and H2 peptide were deleted. | 8 |
| 4 | 548-620 | ΔH1H2 | 5'-terminal fragment containing H1 peptide, and H2 peptide, were deleted. | 9 |
| 5 | 548-614 | ΔH1H2(6) | 5'-terminal fragment containing H1 peptide, H2 peptide and EPDIM, were deleted. | 10 |

Each of the deletion mutants was generated by PCR using a cDNA template encoding the fourth fas-1 domain (SEQ ID NO: 5) (Kim, J.-E. et al., J. Biol. Chem., 275:30907-30915, 2000). Each of the PCR-amplified DNA fragments was cloned into the EcoRV/XhoI sites of the pET-29b(+) vector (Novagen; Madison, Wis.). The mutations were confirmed by sequence analysis, and the deletion mutants were expressed and purified according to a prior method (Kim, J.-E., et al., J. Cell. Biochem., 77:169-178, 2000). Thereafter, the cell adhesion activity of each of the deletion mutants was tested in the same manner as in Example 2.

The results showed that ΔH1H2(6), which is the smallest deletion mutant fragment, still retains endothelial cell adhesion activity (data not shown). This suggests that αvβ3 integrin-interacting motif is present within a fragment corresponding to amino acids 548-614 of SEQ ID NO: 1.

4-2: Identification of αvβ3 Integrin-Interacting Motif Using YH Motif Mutants

Previously, the present inventors reported that an YH motif, which contains tyrosine-histidine residues highly conserved in the fragment corresponding to amino acids 548-614 of SEQ ID NO: 1, and several leucine and isoleucine residues adjacent to the tyrosine-histidine residues, binds to the αvβ5 integrin (Kim, J.-E., et al., J. Biol. Chem., 277:46159-46165, 2002). Thus, the present inventors suspected that the YH motif may also interact with the αvβ3 integrin to mediate endothelial cell adhesion. For this reason, in the present invention, the tyrosine-histidine residues conserved in the fas-1 domains, and/or the leucine and isolucine residues adjacent to the tyrosine-histidine residues, were substituted in various combinations by alanine or serine (Kim, J.-E., et al., J. Biol. Chem. 277:4615946165, 2002)(see FIG. 4b). The amino acid sequences of the prepared YH motif mutants are shown in SEQ ID NO: 17 to SEQ ID NO: 22. The mutations were confirmed by sequence analysis. Then, the substitution mutants were expressed and purified according to a known method (Kim, J.-E., et al., J. Cell. Biochem., 77:169-178, 2000). The substitution mutants were tested for their cell adhesion activity according to the same manner as in Example 2.

The results shown in FIG. 4b confirmed that, in a case of D-IV-AA where the tyrosine-histidine residues highly conserved in the fas-1 domains were substituted with alanine-alanine residues that are hydrophobic amino acids, and in cases of D-IV-L and D-IV-R where the leucine and isoleucine residues adjacent to either side (N- or C-terminal region) of the tyrosine-histidine residues were substituted with a hydrophilic amino acid, serine, cell adhesion activity was equal to those of the fas-1 domain (D-IV) and its fragment (H1H2(6)). Meanwhile, in a case of D-IV-LYHR where all of the isoleucine and leucine residues present in both side of the tyrosin-histidine residues were substituted with serine, cell adhesion activity was reduced to half that of the fas-1 domain. Also, in cases of D-IV-LAA and D-IV-AAR where both the tyrosine-histidine residues and the isoleucine and leucine residues adjacent to either side of the tyrosine-histidine residues were substituted with the alanine-alanine residues and the serin residue, respectively, cell adhesion activity was somewhat lower than those of D-IV-LAA and D-IV-AAR. However, all the substitution mutants showed a higher cell adhesion activity than that of a control. Theses results suggest that not only the tyrosine-histidine residues but also the hydrophobic amino acids with bulky side chains, which are adjacent to both sides of the tyrosine-histidine residues, are required for the adhesion of endothelial cells.

EXAMPLE 5

Assay of Inhibition of Endothelial Cell Adhesion by YH18 Synthetic Peptide

To further confirm that the YH motif within βig-h3 is involved in endothelial cell adhesion, the present inventors performed cell adhesion assay using YH18 synthetic peptides (Kim, J.-E., et al., J. Biol. Chem., 277:4615946165, 2002). The YH18 synthetic peptides, which are derived from the YH motif conserved in all the fas-1 domains of βig-h3, are peptides of 18 amino acids containing tyrosine (or asparagine)-histidine residues and flanking several leucine and isoleucine residues.

Concretely, in this Example, the following YH18 synthetic peptides were used: a YH18 synthetic peptide of SEQ ID NO: 23 derived from the first fas-1 domain of βig-h3 (hereinafter, referred to as "D-I YH18"), a YH18 synthetic peptide of SEQ ID NO: 24 derived from the second fas-1 domain (hereinafter, referred to as "D-II YH18"), a YH18 synthetic peptide of SEQ ID NO: 25 derived from the third fas-1 domain (hereinafter, referred to as "D-III YH18"), and a YH18 synthetic peptide of SEQ ID NO: 26 derived from the fourth fas-1 domain (hereinafter, referred to as "D-IV YH18") (see FIG. 5). As a control peptide, an YH18-con. peptide of SEQ ID NO: 27 was used. All the above peptides had been synthesized by AnyGen Co. Ltd, Kwangju, Korea Thereafter, the present inventors tested whether the YH18 synthetic peptides have the ability to inhibit endothelial cell adhesion in the wells coated with βig-h3.

For this purpose, HUVECs were suspended in medium at a density of $3 \times 10^5$ cells/ml, and each of the YH18 synthetic peptides and the YH-con. peptide was added to 0.1 ml of the cell suspension at concentrations of 100 μM, 300 μM, 500 μM and 1,000 μM, respectively. The peptide-containing cell suspensions were preincubated at 37° C. for 30 minutes. The preincubated cells were added to each well of a 96-well plate precoated with a recombinant βig-h3 His-β-b protein. Then, the cells were tested in the same manner as in Example 2.

Figure 5:
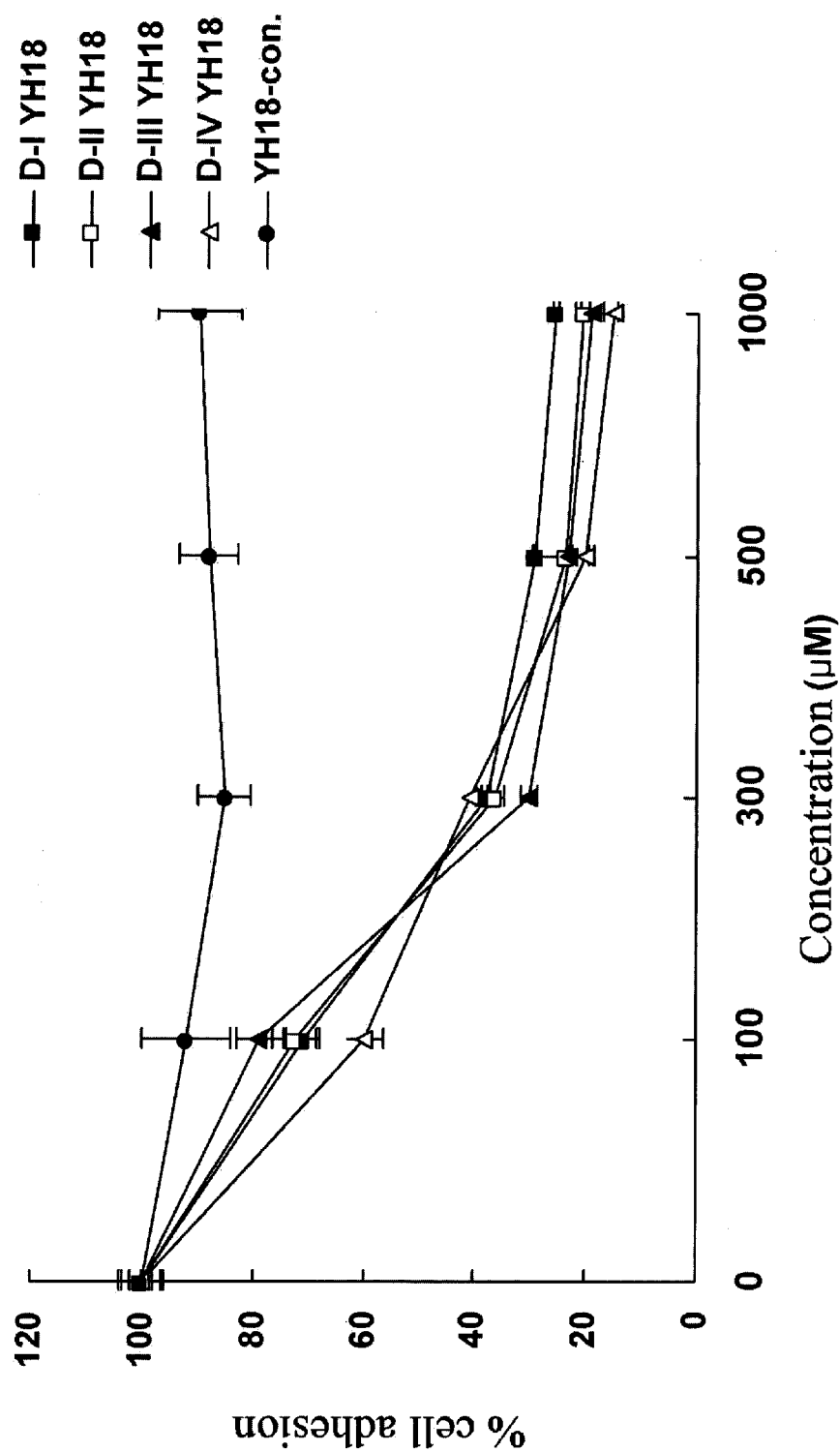
FIG. 5 shows the amino acid sequences of YH18 synthetic peptides derived from each fas-1 domain of βig-h3, and graphically shows the dose-dependent inhibition of HUVECs adhesion to βig-h3 by the peptides.

The results showed that, as shown in FIG. 5, the adhesion of endothelial cells, which is mediated by βig-h3, is inhibited by the YH18 synthetic peptides derived from the fas-1 domains of βig-h3, in a dose-dependent manner. This suggests that the YH motifs are involved in endothelial cell adhesion to βig-h3 through the αvβ3 integrin.

EXAMPLE 6

Reconfirmation of Functional Receptor αvβ3 of Endothelial Cells for βig-h3

To reconfirm that the αvβ3 integrin mediates the adhesion of endothelial cells to βig-h3, a cell adhesion assay was performed using HEK293 cells which had been stably transfected with a human β3 integrin expression vector.

6-1: Cell Adhesion Assay

To construct a human β3 integrin expression vector, RT-PCR was performed using a human placenta poly(A)⁺ RNA as a template, thereby generating a 2.4-kb β3 cDNA (Chandrika, S. K. et al., J. Biol. Chem., 272:16390-16397, 1997). The amplified β3 cDNA was digested with HindIII/XbaI, and then cloned into the pcDNA3 vector (Invitrogen). The resulting vector was named "β3/pcDNA3". Then, 1 μg of the β3/pcDNA3 vector was introduced into HEK293 cells (ATCC, catalog No. CRL 1573) using lipofectamin (Gibco). A control was introduced with a pcDNA3 vector containing no human β3 cDNA. Since all the vectors contain a G418 selection marker, the stable transfected cells were screened using 1 mg/ml of G418. The cell transfected with the β3/pcDNA3 vector was named "β3/293", and the cell transfected with the pcDNA3 vector (control) was named "pc/293". Each of the screened transfectants was incubated in DMEM (Dulbecco's Modified Eagle Medium) containing 10% FBS, streptomycin and penicillin. Then, cell adhesion assay was performed in the same manner as in Example 2.

Figure 6A:
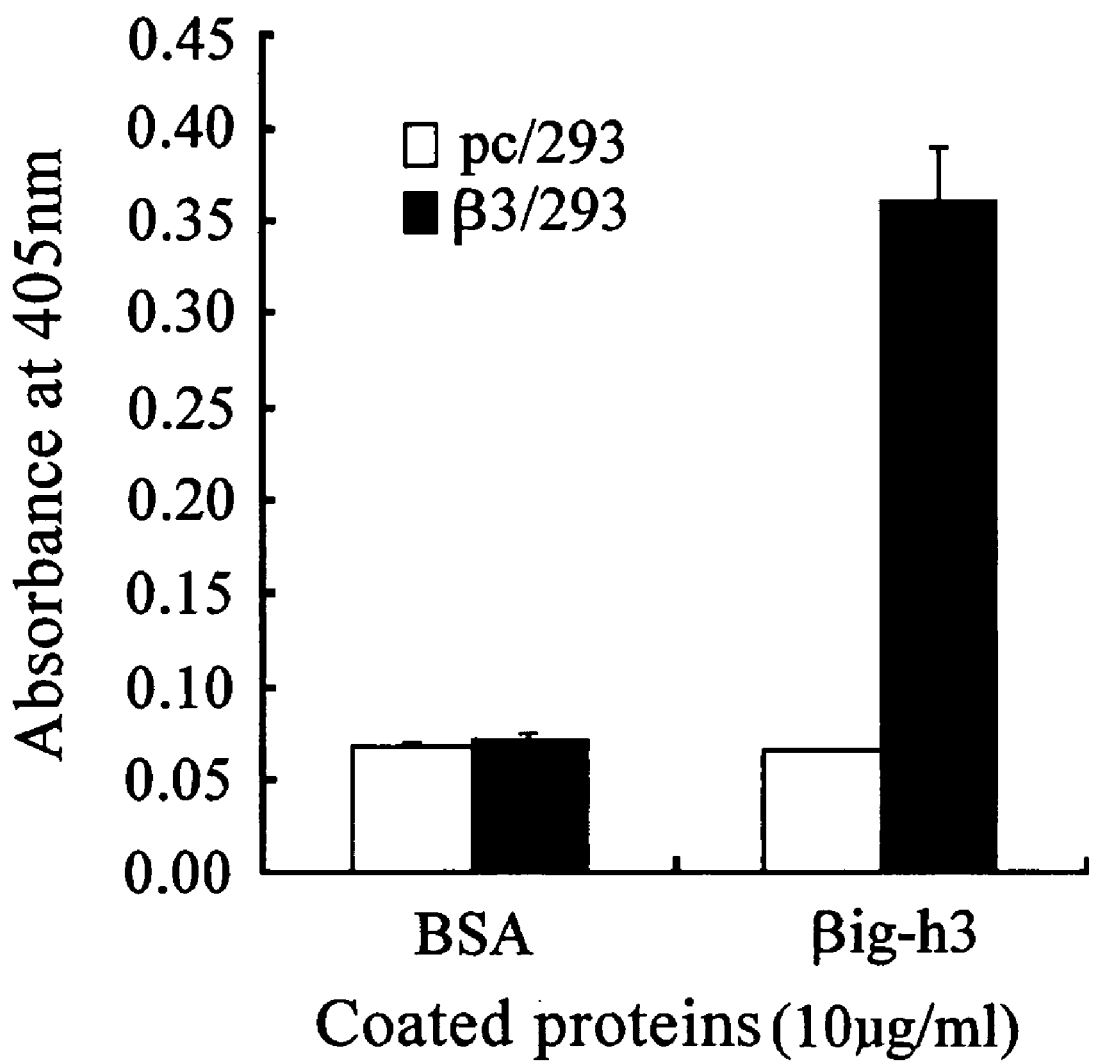
FIG. 6a is a graphic diagram showing the adhesion of HEK293 cells transfected with a β3 integrin expression vector to βig-h3.
    pc/293: HEK293 cells transfected with pcDNA3 vector
    β3/293: HEK293 cells transfected with β3 integrin expression vector

The results showed that, as shown in FIG. 6a, the β3/293 cells were strongly adhered to βig-h3, whereas the pc/293 cells were not adhered to βig-h3, in a similar manner to the plate coated with BSA. This is because the pc/293 cells do not synthesize β3 while producing only αv by themselves and thus do not adhered to βig-h3, but the β3/293 cells can express β3 to produce the αvβ3 integrin.

6-2: Assay of Inhibition of Endothelial Cell Adhesion Using Integrin Function-Blocking Antibodies In the present invention, to further confirm that βig-h3 mediates endothelial cell adhesion through the αvβ3 integrin, cell adhesion assay using antibodies that block the function of integrins was performed in the same manner as in Example 3-1.

Figure 6B:
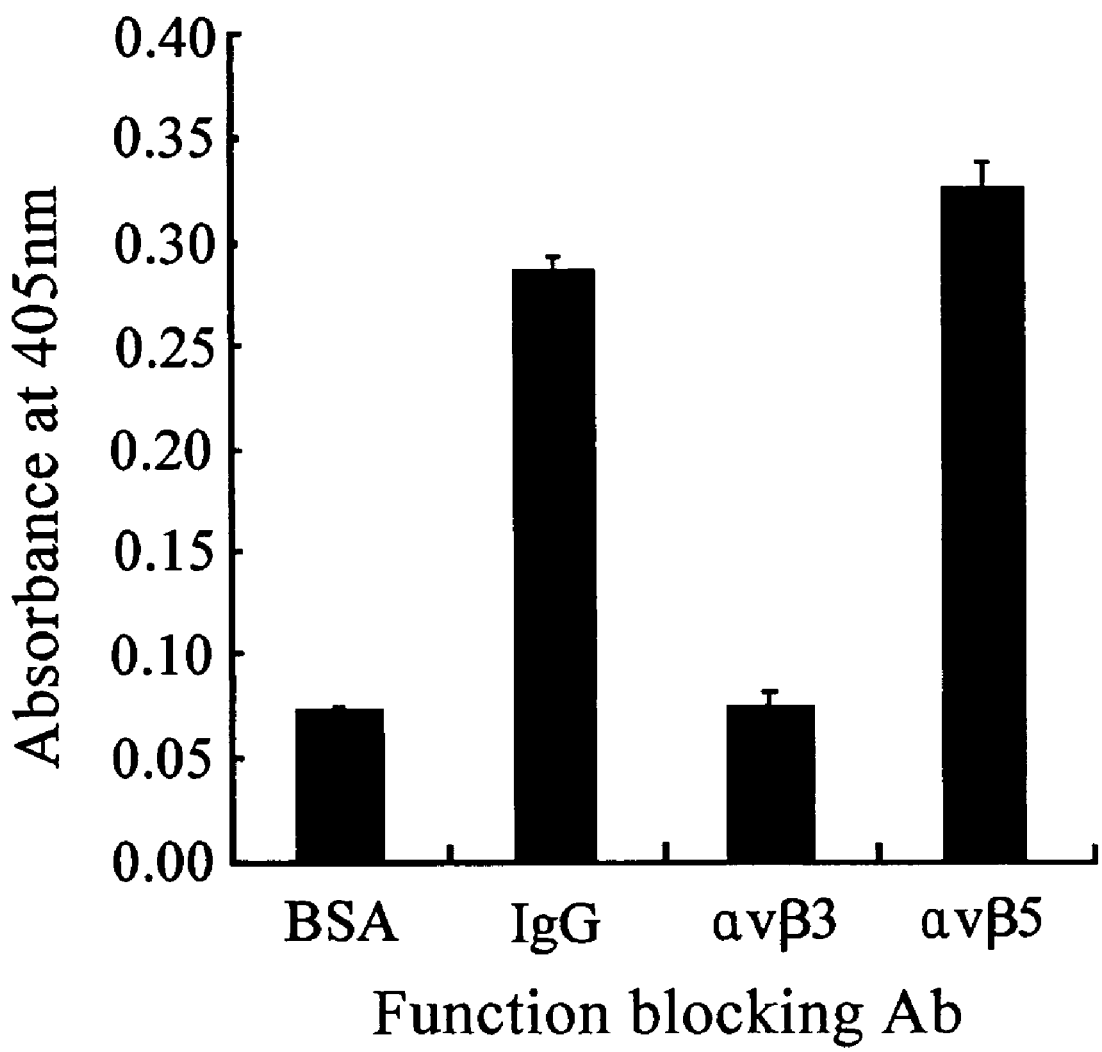
FIG. 6b is a graphic diagram showing the inhibition of β3/293 cell adhesion to βig-h3 coated on the plate by a function-blocking antibody against αvβ3 or αvβ5 integrin.
    BSA: plate coated with BSA
    IgG: treated with mouse IgG
    αvβ3: treated with LM609 (antibody to αvβ3)
    αvβ5: treated with P1F6 (antibody to αvβ5)

The results showed that, as shown in FIG. 6b, the adhesion of β3/293 cells to βig-h3 was inhibited specifically by a function-blocking antibody against the αvβ3 integrin, whereas the adhesion is not inhibited by an antibody to αvβ5.

6-3: Assay of Inhibition of Endothelial Cell Adhesion Using YH18 Synthetic Peptide In Example 5, the present inventors confirmed that the YH18 synthetic peptides inhibit endothelial cell adhesion to βig-h3 through the αvβ3 integrin. Then, the present inventors tested whether the YH18 synthetic peptide also inhibits the adhesion of β3/293 cells to βig-h3. The test was performed in the same manner as in Example 5.

Figure 6C:
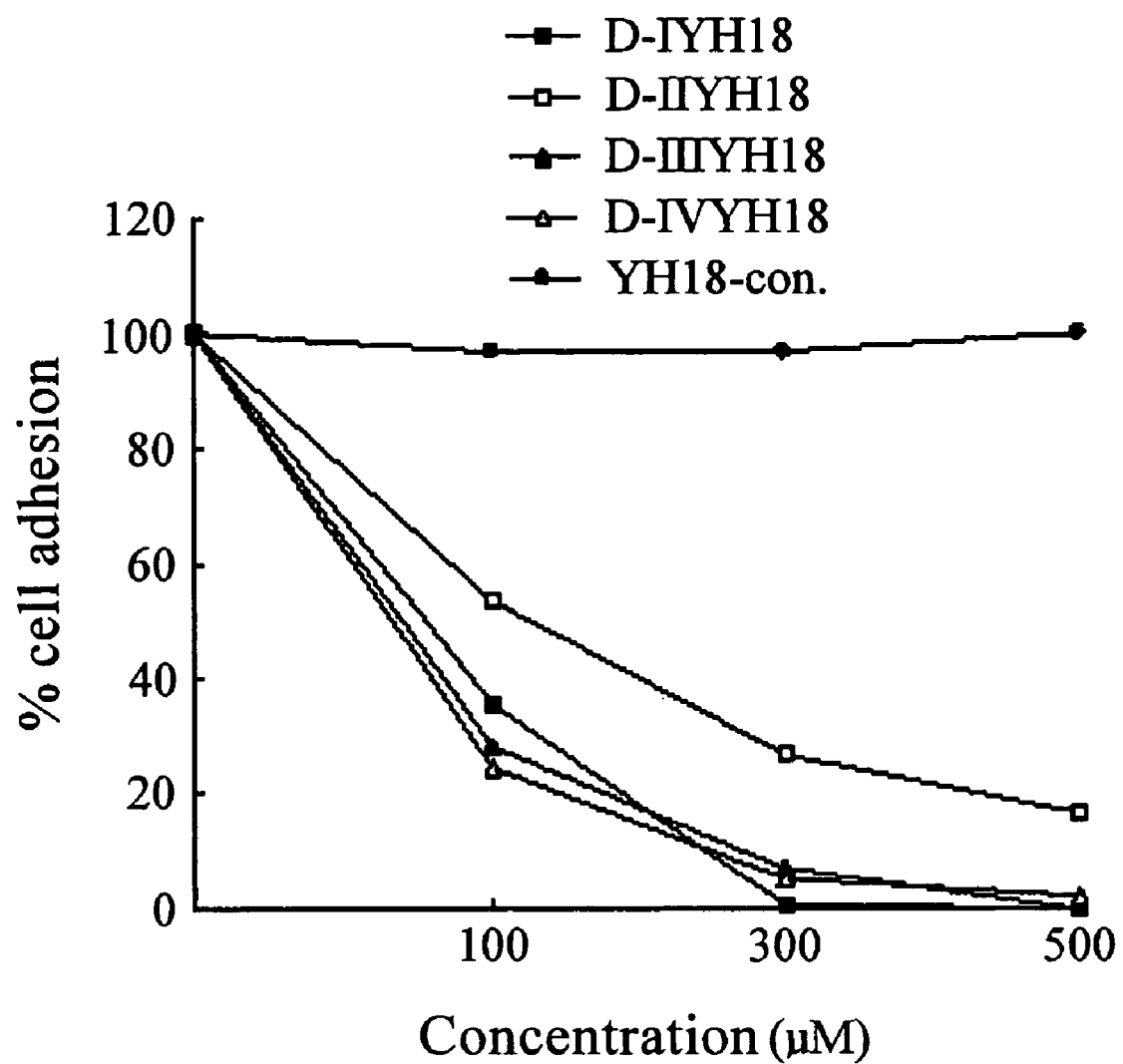
FIG. 6c is a graphic diagram showing the dose-dependent inhibition of β3/293 cell adhesion to βig-h3 coated on the plate by YH18 synthetic peptides.

The results showed that, as shown in FIG. 6c, the YH18 synthetic peptides derived from each of the fas-1 domains inhibit the adhesion of β3/293 to βig-h3 in a dose-dependent manner.

From the above results, it was reconfirmed that the YH motif in each fas-1 domain of βig-h3 mediates endothelial cell adhesion through αvβ3, and a peptide containing the YH motif inhibits the endothelial cell adhesion by interacting with the αvβ3 integrin.

EXAMPLE 7

Assay of Inhibition of Endothelial Cell Migration by YH18 Synthetic Peptide 7-1: Assay of Inhibition of Endothelial Cell Migration Using Integrin Function-Blocking Antibody Firstly, to examine whether βig-h3 is involved in the migration of endothelial cells, the present inventors performed cell migration assay. The cell migration assay was performed in a transwell plate (8 μm pore size, Costar, Cambridge, Mass.). The undersurface of the membrane was coated with the recombinant βig-h3 His-β-b protein (10 μg/ml) prepared in Example 1 at 4° C., and then, blocked for 1 hour at room temperature with PBS buffer containing 2% BSA. Meanwhile, HUVECs were added with an anti-αvβ3 antibody (LM609) or an anti-αvβ5 antibody (P1F6) and preincubated at 37° C. for 30 minutes. A control was added with mouse IgG. Then, the HUVECs preincubated with the antibody were suspended in medium at a density of $3 \times 10^5$ cells/ml, and 0.1 ml of the cell suspension was added to the upper compartment of the filter. The cells were allowed to migrate at 37° C. for 6-8 hours.

Migration was terminated by removing the cells from the upper compartment of the filter with a cotton swab. The filters were fixed with 8% glutaraldehyde and stained with crystal violet. The extent of cell migration was determined by light microscope, and within each well, cell counting was done in nine randomly selected fields HPF (Microscopic high power fields, ×200).

The results showed that the migration of HUVECs was enhanced in those transwells whose undersurface was coated with βig-h3 (data not shown) and this effect was inhibited specifically by an antibody to the αvβ3 integrin but not an antibody to the αvβ5 integrin (see FIG. 7a).

7-2: Assay of Inhibition of Endothelial Cell Migration by YH18 Synthetic Peptide Then, the present inventors examined whether the migration of endothelial cells is inhibited by the YH18 synthetic peptide. For this purpose, a test was performed in the same manner as in Example 7-1 except that 500 µM or 1 mM of an YH18 synthetic peptide represented by SEQ ID NO: 26 instead of the integrin function-blocking antibody was added together in adding the HUVECs suspension to the upper compartment of the membrane. A control to the peptide treatment was treated with 5% DMSO (solvent), and a control to the YH synthetic peptide added with an YH18-con. peptide represented by SEQ ID NO: 27.

Figure 7B:
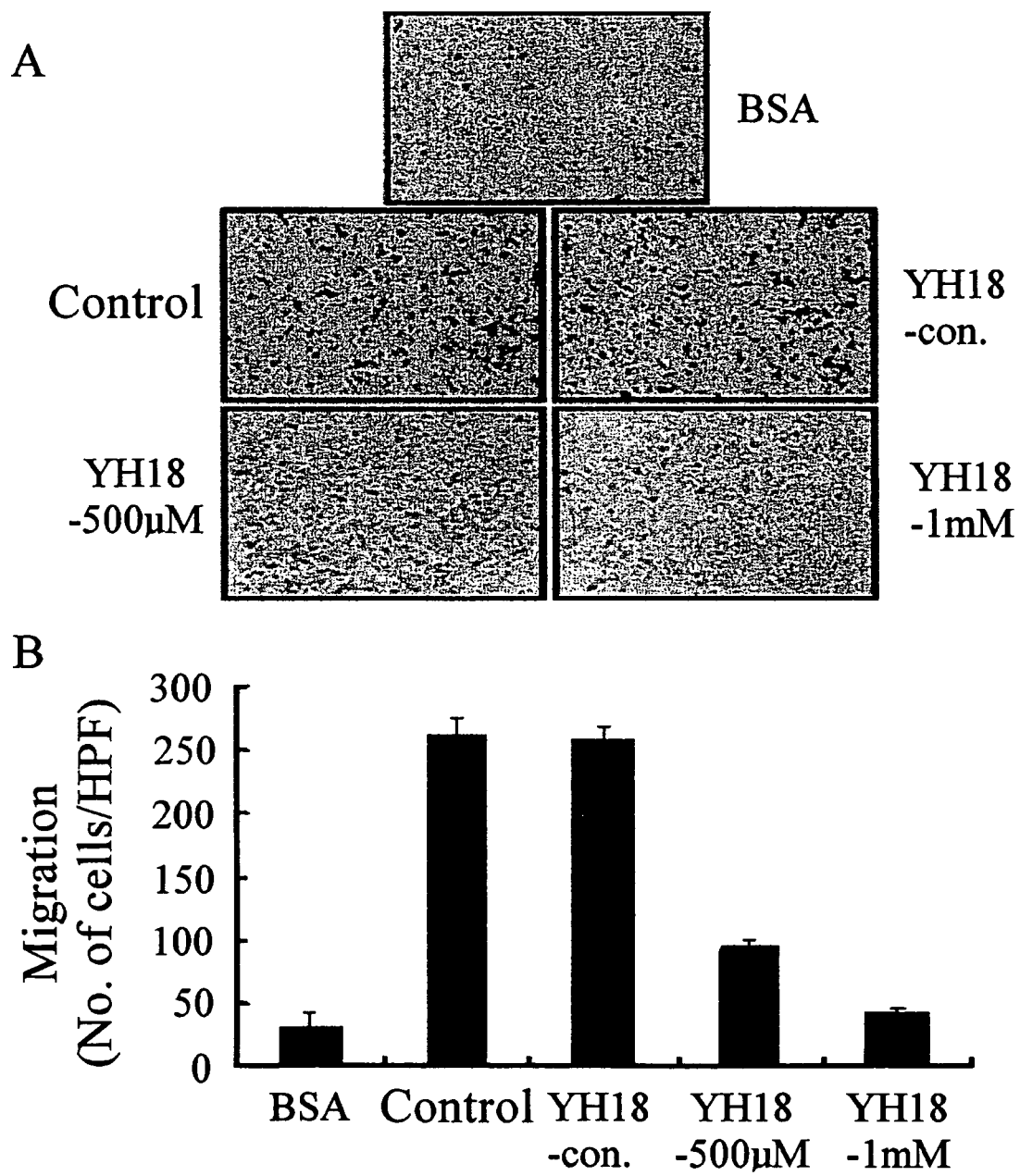
FIG. 7b is a photograph (A) and a graphic diagram (B), which show the inhibition of HUVECs migration toward βig-h3 coated on the plate by an YH18 synthetic peptide.
    BSA: plated with BSA
    control: treated with 5% DMSO
    YH18-con.: treated with YH18-con. peptide (control peptide)
    YH18-500 µM: treated with 500 µM YH18 synthetic peptide
    YH18-1 mM: treated with 1 mM YH18 synthetic peptide

The test results showed that, as shown in FIG. 7b, the YH18 synthetic peptide also inhibited the migration of endothelial cells toward βig-h3. This result suggests that the YH motif of βig-h3 mediates endothelial cell migration through the αvβ3 integrin, and the peptide containing the YH motif inhibits endothelial cell migration by interacting with the βvβ3 integrin.

EXAMPLE 8

Assay of Angiogenesis Inhibition by YH18 Synthetic Peptide 8-1: Endothelial Tube Formation Assay To examine whether the YH motif in the fas-1 domain inhibits angiogensis, the present inventors assayed the effect of the peptide on endothelial tube formation.

First, 100 µl of Matrigel (Chemicon, International Inc, Temecula, Calif.) was added to each well of a 96-well plate and allowed to polymerize. HUVECs were suspended in medium at a density of $3\times10^5$ cells/ml, and 0.1 ml of the cell suspension was added to each well of the well plate coated with Matrigel. At this time, 500 µM or 1 mM of the YH18 synthetic peptide represented by SEQ ID NO: 26 was added together. A control to peptide treatment was treated with 5% DMSO (solvent), and a control to the YH18 synthetic peptide was treated with the YH18-con. peptide represented by SEQ ID NO: 27. Thereafter, the cells were incubated at 37° C. for 16-18 hours. The cells were photographed, and endothelial tubes were counted and averaged.

The results showed that, as shown in FIG. 8a, the YH18 synthetic peptide selectively inhibited the dose-dependent manner. The $IC_{50}$ of the YH18 synthetic peptide was 500 µM.

8-2: Matrigel Plug Assay

In the present invention, the angiogenesis-inhibitory effect of the YH18 synthetic peptide, which had been proven in vitro assay according to Example 8-1, was assayed in vivo. An in vivo Matrigel plug assay was performed according to the method described by Maeshima, Y. et al., J. Biol. Chem., 275:23745-23750, 2000. 5-6 week old male C57/BL6 mice purchased from Hyochang scientific company, Korea, were used.

First, Matrigel (BD Biosciences, MA) was mixed with 20 units/ml heparin, 150 ng/ml bFGF (basic fibroblast growth factor, R&D system, International, Inc), and a YH18 synthetic peptide represented by SEQ ID NO: 26. As a control to the YH18 synthetic peptide, an YH18-con. peptide was used, and a control to peptide treatment was treated with 5% DMSO (solvent). The Matrigel mixture was injected subcutaneously to the C57/BL6 mice. After 7 days, the mice were sacrificed, and the Matrigel plugs were removed and fixed in 4% paraformaldehyde. The Matrigel plugs were buried in paraffin, sectioned and stained with H&E. Their sections were examined by light microscope, the number of blood vessels from 4-6 HPF (high power fields; ×200) was counted and averaged. Each group consisted of 3 or 4 Matrigel plugs.

Figure 8B:
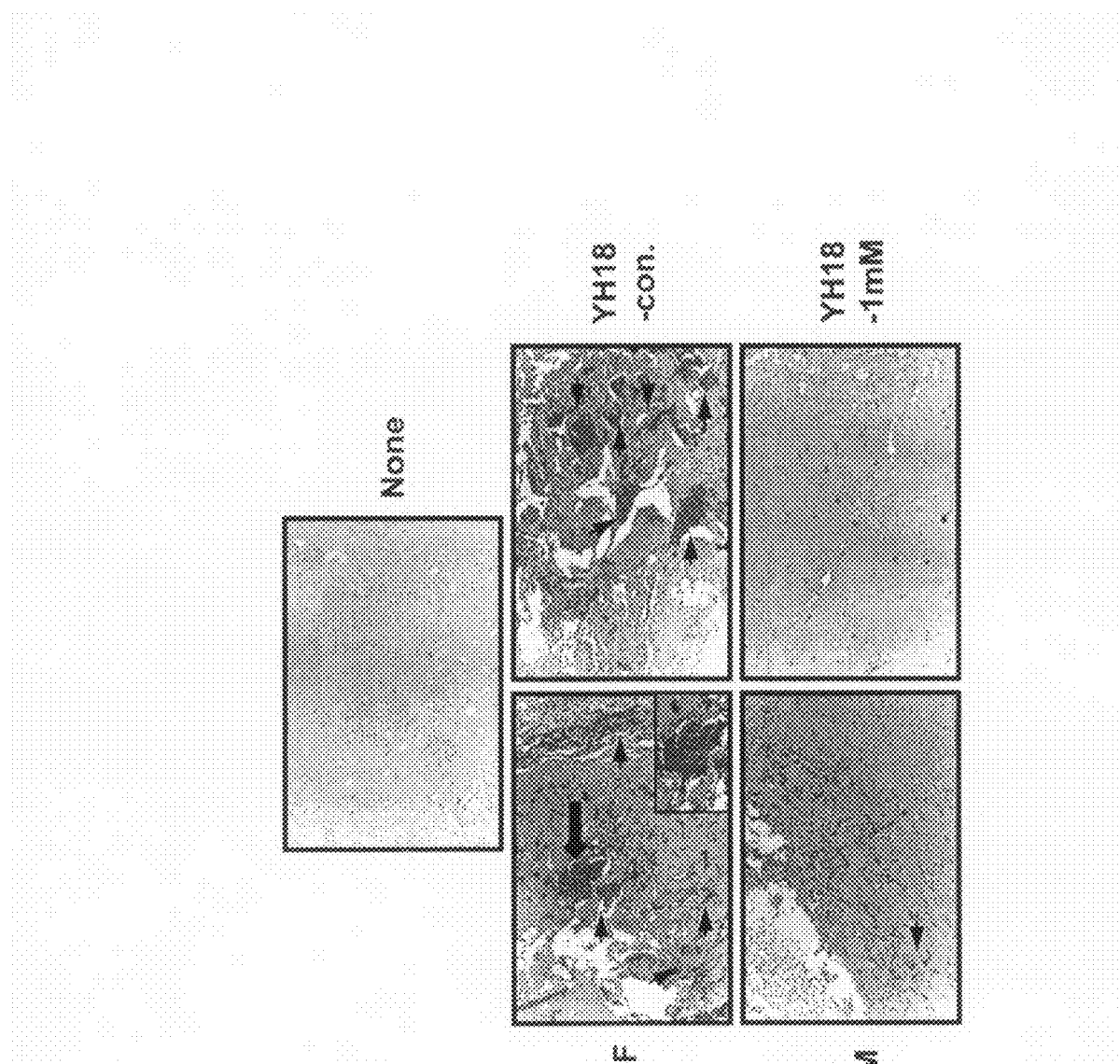
FIG. 8b is a photograph (A) showing the inhibition of angiogenesis by the YH18 synthetic peptide, a photograph (B) showing a section stained with H&E, and a graphic diagram (C) showing the result of measurement for the number of blood vessels.

The results showed that a significant reduction in the number of blood vessels was observed at 500 µM of the YH18 synthetic peptide and a complete inhibition of angiogenesis was observed at 1 mM of the peptide (see A of FIG. 8b). Also, the result of observation of the section was the same as described above (see B and C of FIG. 8b).

These results suggest that the peptide containing the YH motif inhibits angiogenesis both in vitro and in vivo.

APPLICATION EXAMPLE 1

Cancers

Angiogenesis is an essential stage in the growth and metastasis of cancer cells (Weidner, N. et al., *N. Engl. J. Med.*, 324:1-8, 1991). Tumors are supplied with nutrients and oxygen necessary for their growth and proliferation through new blood vessels, and also new blood vessels invaded by tumors provides an opportunity for cancer cells to enter the blood circulation, thereby causing the metastasis of the cancer cells (Folkman and Tyler, *Cancer Invasion and Metastasis*, Biologic mechanisms and Therapy (S. B. Day ed.), Raven press, New York, 94-103, 1977; Polverini P. J. *Critical Reviews in Oral Biology*, 6(3):230-247, 1995). If angiogenesis does not occur, the tumors will remain in a resting state and will no longer grow (Folkman and Tyler, *Cancer Invasion and Metastasis*, Biologic mechanisms and Therapy (S. B. Day ed.), Raven press, New York, 94-103, 1977). However, as angiogenesis in cancer tissues develops, cancer cell metastasis toward other tissues occurs (Weidner, N. et al., *N. Engl. J. Med.*, 324:1-8, 1991). The metastasis of cancer cells by blood flow rarely occurs through preexisting blood vessels but mainly occurs at sites where angiogenesis actively occurs. In other words, cancer cells flow out through the incomplete walls of blood vessels, or flows out through the basement membrane of blood vessel walls when the basement membrane is degraded by the action of protease, thereby causing systemic metastasis. In some cases of systemic metastasis, endothelial cells being proliferated cause cancer cells to directly migrate into new blood vessels, thereby causing systemic metastasis. Accordingly, the inventive composition for the inhibition of angiogenesis, which contains the YH motif-containing peptide as an active ingredient, has an excellent angiogenesis inhibitory effect, and thus, is highly effective in the prevention of metastasis and the treatment of various cancers.

APPLICATION EXAMPLE 2

Arthritis

Arthritis is an autoimmune disorder. However, a chronic inflammation, which is formed in the synovial cavity between joints during the progression of arthritis, induces angiogenesis to destroy cartilages. Arthritis includes infectious arthritis, degenerative arthritis, rheumatoid arthritis, and arthritis caused by femoral head avascular necrosis, ankylosing spondylitis and congenital malformation. Regardless of the cause of arthritis, the chronic inflammation formed in the synovial cavity between joints during the progression of arthritis is known to induce angiogenesis. It is characterized in that new capillary vessels invade joint to cause damage to cartilages (Koch A. E. et al., *Arth. Rheum.*, 29:471-479, 1986; Stupack D. G. et al., *J. Med. Biol. Rcs.*, 32:578-281, 1999; Koch A. E., *Arthritis Rheum.*, 41:951-962, 1998). In this case, it has been reported that an inflammatory response, which occurs in several steps depending the kind of diseases to destroy cartilages, plays an important role in the progression of the disease, and the formation of angiogenesis into joints acts as an important pathological mechanism (Colville-Nash, P. R. et al., *Ann. Rheum. Dis.*, 51, 919-925, 1992; Eisenstein, R., *Pharmacol. Ther.*, 49:1-19, 1991). For the treatment of arthritis, it is preferred to inhibit pains and inflammations so as to reduce the destruction rate of joints or muscles and minimize loss of their function. Accordingly, the inventive composition for the inhibition of angiogenesis is highly effective in the prevention of arthritis progression and in the treatment of arthritis.

APPLICATION EXAMPLE 3

Psoriasis

Psoriasis is a skin disease that involves papules and silver white scars. It is generally a chronic proliferative disorder whose deterioration and improvement are repeated. Also, its cause is not yet identified, but it is known that the formation of new blood cells on pathological lesions or non-lesions, and also the infiltration of immune cells, such as neutrophil, as a result of an increase in blood vessel permeability, play an important role in the deterioration of psoriasis (Bhushan, M. et al., *Br. J. Dermatol*, 141:1054-1060, 1999). In normal persons, keratinocytes are proliferated one time a month, but in patients with psoriasis, keratinocytes are proliferated one time a week. Since much blood is necessary for this frequent proliferation, angiogenesis will necessarily occur fast (Folkman J. *J. Invest. Dermatol.*, 59:4048, 1972). Accordingly, the inventive composition for the inhibition of angiogenesis is effective in the treatment of psoriasis.

APPLICATION EXAMPLE 4

Diabetic Eye Diseases

Ophthalmic diseases by which several million persons each year in the world lose their sight are also caused by angiogenesis (Jeffrey M. I. et al., *J. Clin. Invest.*, 103:1231-1236, 1999; Stupack D. G. et al., *J. Med. Biol. Rcs.*, 32:578-281, 1999). Typical examples of the ophthalmic diseases include age-related macular degeneration(AMD), diabetic retinopathy, retinopathy of prematurity, neovascular glaucoma, and corneal diseases caused by angiogenesis (Adamis A. P. et al., *Angiogenesis*, 3:9-14, 1999). Among them, the diabetic eye disease is one of main diabetic complications capable of causing loss of eyesight, and occurs in a patient with long diabetic duration regardless of the regulation of blood glucose. With a recent improvement in diabetic therapy, the lifespan of diabetic patients is extended while diabetic retinopathy shows a tendency to increase. Thus, the diabetic retinopathy is the leading cause of adult blindness in Western Europe and also Korea. The diabetic retinopathy develops due to the functional reduction of retinal circulation so that angiogenesis spreads along the internal surface and posterior hyaloid membrane of the retina while blood vessels invade the hyaloid, or bleeding occurs, resulting in blindness. Particularly, it has been reported that diabetic eye diseases, such as diabetic retinopathy, are caused by rapid progression of angiogenesis (Favard, C. et al., *Diabetes, Metab.*, 22:268-273, 1996). Accordingly, the inventive composition for the inhibition of angiogenesis is highly effective in the prevention and treatment of diabetic eye diseases.

APPLICATION EXAMPLE 5

Arterial Sclerosis

Sclerosis of the arteries means diseases where arterial walls become thicker to lose their elasticity. It is classified into three morphological categories, the most frequent and important category of which is atherosclerosis caused by the formation of atheroma in the arteries. The atheroma, which is formed of cholesterol and cholesterol ester and enclosed in a fibrous membrane, covers the tunica intima of the arteries while the lumen of arterial walls becomes narrower to block the blood flow of distal organs, thereby causing ischemic injury to the organs. If the atheroma is formed in the main artery, it then weakens the arterial walls to cause aneurysm, blood vessel disruption and thrombosis. In this case, it has been reported that the formation of new blood vessel within atheroma (angiogenesis) plays an important role in weakening the blood vessel walls (Hoshiga, M. et al., *Circ. Res.*, 77:1129-1135, 1995; Kahlon, R. et al., *Can. J. Cardiol.*, 8:60-64, 1992; George, S. J., *Curr. Opin. Lipidol.*, 9:413-423, 1998). Accordingly, the inventive composition for the inhibition of angiogenesis is highly effective in the prevention of severe complications that can be caused by arterial sclerosis.

APPLICATION EXAMPLE 6

Inflammation

Inflammation, which is a response of a living tissue to injury, can be caused by various factors, such as infection and trauma, but show substantially similar changes regardless of its cause and response tissue. Such changes include an increase in blood flow, an increase in permeability of blood vessel walls, and the infiltration of white blood cells, in which all the changes are known to be caused by angiogenesis (Jackson, J. R. et al., *FASEB, J.*, 11:457-465, 1997). Although inflammation is a repairing mechanism of injury and thus not a harmful response, it can cause the injury and deformation of tissues when it excessively occurs or inappropriately occurs as in autoimmune diseases. In regulating such an excessive or inappropriate inflammatory response, the inventive composition for the inhibition of angiogenesis is effective.

INDUSTRIAL APPLICABILITY

As described above, the peptide according to the present invention interacts with the αvβ3 integrin of endothelial cells, so that it inhibits the adhesion and migration of endothelial cells and also shows an excellent angiogenesis-inhibitory effect. Accordingly, the inventive peptide is useful for the inhibition of endothelial cell adhesion, endothelial cell migration, and/or angiogenesis. In addition, it is useful for the treatment or prevention of various angiogensis-related diseases.

What is claimed is:

1. A method for inhibiting endothelial cell adhesion, endothelial cell migration and/or angiogenesis, comprising administering to a subject in need thereof an effective amount of:
   an isolated peptide comprising an amino acid sequence represented by (I, D, E or K)-(E, A or Q)-L-(L, R or A)-(N, D or S)-(A, L, K or I)-(L or Y)-(R, N, L or K)-(Y or N)-H\-(M, I or G)-(V, L, Q or G)-(G, K, T or D)-(R, S, L or E)-(R, A, E or I)-(V, M, T or L)-(L, C or V)-(T, A, G or S);
   wherein said subject in need thereof has an angiogenesis-related disease selected from cancer and rheumatoid arthritis.

2. The method of claim 1, wherein the isolated peptide comprises an amino acid sequence selected from the group consisting of SEQ ID NO: 23 to SEQ ID NO: 26.

3. A method for inhibiting endothelial cell adhesion, endothelial cell migration and/or angiogenesis, comprising administering to a subject in need thereof an effective amount of an isolated peptide comprising an amino acid sequence selected from the group consisting of SEQ ID NO: 11 to SEQ ID NO: 16, wherein said subject in need thereof has an angiogenesis-related disease selected from cancer and rheumatoid arthritis.

4. The method of claim 3, wherein the isolated peptide comprises an amino acid sequence selected from the group consisting of SEQ ID NO: 17 to SEQ ID NO: 22.

5. A method for the treatment of an angiogenesis-related disease, comprising administering to a subject in need thereof an effective amount of:
   an isolated peptide comprising an amino acid sequence represented by (I, D, E or K)-(E, A or Q)-L-(L, R or A)-(N, D or S)-(A, L, K or I)-(L or Y)-(R, N, L or K)-(Y or N)-H\- (M, I or G)-(V, L, Q or G)-(G, K, T or D)-(R, S, L or E)-(R, A, E or I)-(V, M, T or L)-(L, C or V)-(T, A, G or S), wherein the angiogenesis-related disease is selected from the group consisting of: cancer and rheumatoid arthritis.

6. The method of claim 5, wherein the isolated peptide comprises an amino acid sequence selected from the group consisting of SEQ ID NO: 23 to SEQ ID NO: 26.

7. A method for the treatment of an angiogenesis-related disease, comprising administering to a subject in need thereof an effective amount of:
   an isolated peptide comprising an amino acid sequence selected from the group consisting of SEQ ID NO: 11 to SEQ ID NO: 16.

8. The method of claim 7, wherein the isolated peptide comprises an amino acid sequence selected from the group consisting of SEQ ID NO: 17 to SEQ ID NO: 22.

9. The method of claim 5, wherein the angiogenesis-related disease is cancer.

10. The method of claim 5, wherein the angiogenesis-related disease is rheumatoid arthritis.

* * * * *